(12) United States Patent
Bachelet et al.

(10) Patent No.: US 9,522,396 B2
(45) Date of Patent: Dec. 20, 2016

(54) APPARATUS AND METHOD FOR AUTOMATIC DETECTION OF PATHOGENS

(75) Inventors: Ido Bachelet, Modiin (IL); Joseph Joel Pollak, Alon Shvut (IL); Daniel Levner, Toronto (CA); Yonatan Bilu, Jerusalem (IL); Noam Yorav-Raphael, Efrat (IL)

(73) Assignee: S.D. Sight Diagnostics Ltd., Jerusalem (IL)

( * ) Notice: Subject to any disclaimer, the term of this patent is extended or adjusted under 35 U.S.C. 154(b) by 1247 days.

(21) Appl. No.: 13/338,291

(22) Filed: Dec. 28, 2011

(65) Prior Publication Data

US 2012/0169863 A1  Jul. 5, 2012

Related U.S. Application Data

(60) Provisional application No. 61/427,809, filed on Dec. 29, 2010.

(51) Int. Cl.
*B01L 3/00* (2006.01)
*G01N 21/59* (2006.01)
(Continued)

(52) U.S. Cl.
CPC ..... *B01L 3/502715* (2013.01); *G01N 15/1463* (2013.01); *G01N 21/5907* (2013.01);
(Continued)

(58) Field of Classification Search
CPC ......... C12Q 1/689; C12Q 1/04; C12Q 1/6837; C12Q 1/6893; C12Q 1/6895; G01N 15/1475; G06T 2207/30024; G06T 7/0012

See application file for complete search history.

(56) References Cited

U.S. PATENT DOCUMENTS 4,700,298 A   10/1987  Palcic et al.
4,803,352 A   2/1989   Bierleutgeb
(Continued)

FOREIGN PATENT DOCUMENTS

EP      0183717       11/1989
GB      2 329 014 A    3/1999
(Continued)

OTHER PUBLICATIONS

Tek, F. Boray, Andrew G. Dempster, and Izzet Kale. "Parasite detection and identification for automated thin blood film malaria diagnosis." Computer Vision and Image Understanding 114.1 (2010): 21-32.

(Continued)

*Primary Examiner* — Sally Merkling
(74) *Attorney, Agent, or Firm* — Wiggin and Dana LLP; Gregory S. Rosenblatt

(57) ABSTRACT

The invention discloses an apparatus and method for automatic detection of pathogens within a sample. The apparatus and method are especially useful for high-throughput and/or low-cost detection of parasites with minimal need for trained personnel. The invention entails automated microscopic data acquisition, and performing image processing of images captured from a sample using classification algorithms. Visual classification features of structures are extracted from the image and compared to visual classification features associated with known pathogens. A determination is reached whether a pathogen is present in the sample; and if present, the pathogen may be identified to a pathogen species. Diagnosis is rapid and does not require medically trained personnel.

20 Claims, 9 Drawing Sheets

(51) Int. Cl.
    *G01N 21/64*   (2006.01)
    *G01N 15/14*   (2006.01)
    *G01N 21/23*   (2006.01)
    *G01N 15/10*   (2006.01)

(52) U.S. Cl.
    CPC .. *G01N 21/6458* (2013.01); *B01L 2300/0816* (2013.01); *B01L 2300/0864* (2013.01); *G01N 21/23* (2013.01); *G01N 2015/1006* (2013.01); *G01N 2021/6419* (2013.01); *G01N 2021/6421* (2013.01)

(56) References Cited

U.S. PATENT DOCUMENTS

| | | |
|---|---|---|
| 4,902,101 A | 2/1990 | Fujihara et al. |
| 5,470,751 A | 11/1995 | Sakata et al. |
| 5,663,057 A | 9/1997 | Drocourt et al. |
| 5,782,770 A | 7/1998 | Mooradian et al. |
| 5,932,872 A | 8/1999 | Price |
| 5,985,595 A | 11/1999 | Krider et al. |
| 6,005,964 A * | 12/1999 | Reid et al. ............ 382/133 |
| 6,101,404 A | 8/2000 | Yoon et al. |
| 6,320,979 B1 | 11/2001 | Melen |
| 6,350,613 B1 | 2/2002 | Wardlaw et al. |
| 6,799,119 B1 | 9/2004 | Voorhees et al. |
| 6,834,237 B2 | 12/2004 | Noergaard et al. |
| 6,955,872 B2 | 10/2005 | Maples et al. |
| 7,034,883 B1 | 4/2006 | Rosenqvist |
| 7,369,696 B2 | 5/2008 | Arini et al. |
| 7,417,213 B2 | 8/2008 | Krief et al. |
| 7,490,085 B2 | 2/2009 | Walker et al. |
| 7,706,862 B2 | 4/2010 | Alfano et al. |
| 7,998,435 B2 | 8/2011 | Reed |
| 8,105,554 B2 | 1/2012 | Kanigan et al. |
| D655,421 S | 3/2012 | Lee et al. |
| 2002/0028471 A1 | 3/2002 | Oberhardt |
| 2003/0017085 A1 | 1/2003 | Kercso et al. |
| 2003/0170613 A1 | 9/2003 | Straus |
| 2003/0224522 A1* | 12/2003 | de Jong ........... A61K 47/48007 435/458 |
| 2003/0231791 A1 | 12/2003 | Torre-Bueno et al. |
| 2004/0132171 A1 | 7/2004 | Rule et al. |
| 2004/0241677 A1* | 12/2004 | Lin et al. ............ 435/6 |
| 2006/0003458 A1 | 1/2006 | Golovchenko et al. |
| 2006/0063185 A1 | 3/2006 | Vannier |
| 2006/0190226 A1 | 8/2006 | Jojic et al. |
| 2006/0222567 A1 | 10/2006 | Kloepfer et al. |
| 2007/0250301 A1* | 10/2007 | Vaisberg ............ G01N 15/1475 703/11 |
| 2008/0059135 A1 | 3/2008 | Murugkar et al. |
| 2008/0118399 A1 | 5/2008 | Fleming |
| 2008/0260369 A1* | 10/2008 | Ibaraki .......... H04N 5/232 396/55 |
| 2009/0128618 A1 | 5/2009 | Fahn et al. |
| 2009/0191098 A1 | 7/2009 | Beard et al. |
| 2009/0269799 A1 | 10/2009 | Winkelman et al. |
| 2009/0291854 A1 | 11/2009 | Wiesinger-Mayr et al. |
| 2010/0068747 A1 | 3/2010 | Herrenknecht |
| 2010/0112631 A1 | 5/2010 | Hur et al. |
| 2010/0120129 A1 | 5/2010 | Amshey et al. |
| 2010/0136556 A1 | 6/2010 | Friedberger et al. |
| 2010/0136570 A1 | 6/2010 | Goldberg et al. |
| 2010/0295998 A1 | 11/2010 | Sakai et al. |
| 2010/0300563 A1 | 12/2010 | Ramunas et al. |
| 2011/0144480 A1 | 6/2011 | Lu et al. |
| 2011/0275111 A1 | 11/2011 | Pettigrew et al. |
| 2012/0021951 A1 | 1/2012 | Hess et al. |
| 2012/0030618 A1 | 2/2012 | Leong et al. |
| 2012/0058504 A1 | 3/2012 | Li et al. |
| 2012/0092477 A1 | 4/2012 | Kawano et al. |

FOREIGN PATENT DOCUMENTS

| | | |
|---|---|---|
| JP | 2004144526 | 5/2004 |
| JP | 2004257768 | 9/2004 |
| WO | 0052195 | 9/2000 |
| WO | 02/33400 A1 | 4/2002 |
| WO | 2003073365 | 9/2003 |
| WO | 2004111610 | 12/2004 |
| WO | 2006121266 | 11/2006 |
| WO | 2008063135 | 5/2008 |
| WO | 2010126903 | 11/2010 |
| WO | 2011076413 | 6/2011 |
| WO | 2011143075 | 11/2011 |
| WO | 2012000102 | 1/2012 |
| WO | 2012030313 | 3/2012 |

OTHER PUBLICATIONS

Kumar, Amit, et al. "Enhanced identification of malarial infected objects using Otsu algorithm from thin smear digital images." Int. J. Lat. Res. Sc. Tech 1 (2012): 159-163.

Moon, Seunghyun, et al. "An image analysis algorithm for malaria parasite stage classification and viability quantification." PloS one 8.4 (2013): e61812.

Mendiratta, D. K., et al. "Evaluation of different methods for diagnosis of P. falciparum malaria." Indian journal of medical microbiology 24.1 (2006): 49-51.

Pasini, Erica M., et al. "A novel live-dead staining methodology to study malaria parasite viability." Malaria journal 12.1 (2013): 190.

Price, Jeffrey H., and David A. Gough. "Comparison of phase—contrast and fluorescence digital autofocus for scanning microscopy." Cytometry 16.4 (1994): 283-297.

Sun, Yu, Stefan Duthaler, and Bradley J. Nelson. "Autofocusing algorithm selection in computer microscopy." Intelligent Robots and Systems, 2005.(IROS 2005). 2005 IEEE/RSJ International Conference on. IEEE, 2005.

Vink, J. P., et al. "An automatic vision—based malaria diagnosis system."Journal of microscopy 250.3 (2013): 166-178.

Yao, L. N., et al. "Pathogen identification and clinical diagnosis for one case infected with Babesia." Zhongguo ji sheng chong xue yu ji sheng chong bing za zhi, Chinese journal of parasitology & parasitic diseases 30.2 (2012): 118-121.

"Malaria Diagnostics Technology and Market Landscape", 2nd edition, UNITAID, Jul. 2014.

Keiser, J., et al. "Acridine Orange for malaria diagnosis: its diagnostic performance, its promotion and implementation in Tanzania, and the implications for malaria control." Annals of tropical medicine and parasitology, 96.7 (2002): 643-654.

Joanny, Fanny, Jana Held, and Benjamin Mordmüller. "In vitro activity of fluorescent dyes against asexual blood stages of Plasmodium falciparum." Antimicrobial agents and chemotherapy 56.11 (2012): 5982-5985.

Biéler, Sylvain, et al. "Improved detection of Trypanosoma brucei by lysis of red blood cells, concentration and LED fluorescence microscopy." Acta tropica 121.2 (2012): 135-140.

Shute, G. T., and T. M. Sodeman. "Identification of malaria parasites by fluorescence microscopy and acridine orange staining." Bulletin of the World Health Organization, 48.5 (1973): 591-159.

Centers for Disease Control and Prevention. "DPDx—Laboratory Identification of Parasitic Diseases of Public Health Concern", <http://www.cdc.gov/dpdx/diagnosticProcedures/blood/microexam.html>, Nov. 29, 2013.

Laboratory diagnosis of blood-borne parasitic diseases: approved guideline. NCCLS, 2000.

Jager, M. M., et al. "Five-minute Giemsa stain for rapid detection of malaria parasites in blood smears." Tropical doctor, 41.1 (2011): 33-35.

Wright, James H. "A rapid method for the differential staining of blood films and malarial parasites." The Journal of medical research 7.1 (1902): 138.

Kawamoto, F. and P. F. Billingsley. "Rapid diagnosis of malaria by fluorescence microscopy." Parasitology today 8.2 (1992): 69-71.

Parasight Ltd, WO 2012/090198 A3, WIPO International Publication, "An Apparatus and Method for Automatic Detection of Pathogens," published Nov. 15, 2012, including International Search Report mailed Jul. 27, 2012.

(56) References Cited

OTHER PUBLICATIONS

F. Kawamoto, P.F. Billingsley, Rapid diagnosis of malaria by fluorescence microscopy, Parasitology Today, vol. 8, Issue 2, Feb. 1992, pp. 69-71, ISSN 0169-4758, http://dx.doi.org/10.1016/0169-4758(92)90093-H. (http://www.sciencedirect.com/science/article/pii/016947589290093H).

Kawamoto, Fumihiko, "Rapid diagnosis of malaria by fluorescence microscopy with light microscope and interference filter". The Lancet, vol. 337, pp. 200-202, Jan. 26, 1991.

\* cited by examiner

APPARATUS AND METHOD FOR AUTOMATIC DETECTION OF PATHOGENS

CROSS-REFERENCE TO RELATED APPLICATIONS

The invention derives priority from U.S. Provisional Patent application Ser. No. 61/427,809, filed 29 Dec. 2010, the entirety of which is incorporated herein by reference.

FIELD OF THE INVENTION

The present invention relates to the field of medical devices. More particularly, the invention relates to an apparatus and method for automatically detecting and identifying pathogens, and particularly parasites, in bodily fluid or tissue samples.

BACKGROUND OF THE INVENTION

To date, when a sample of bodily fluid is collected from an individual for testing of the presence of a parasitic infection, best results are obtained when the sample is smeared on a slide, stained and viewed under a microscope. Only trained medical personnel having sufficient experience are able to perceptively detect and correctly identify the presence of parasitic infection.

This process is labor intensive, as it is performed manually, and thus a low throughput is achieved. PCR or immunological testing may be performed as well. These processes are not suited for general health clinics which may be located in third-world countries, and thus may not have proper laboratory equipment for preparing a sample, viewing it, or testing it.

The need exists for an apparatus which automates identification of parasitic or microbial infection, allowing rapid diagnosis. Such an apparatus is essential especially in locations which may not have trained medical personnel or a full-laboratory for processing of bodily fluids, or where high-throughput screening is desired.

Additionally, blood banks worldwide do not have the capability to test blood donations for many parasitic infections. While typically, some bacterial and viral infections, such as hepatitis, HIV, and others, are tested for, there are currently no rapid tests in use for parasitic infection of blood donations, other than for detection of a single parasitic species, *Trypanosoma cruzi*, which causes Chaggas Disease.

To exemplify the need, there are no established rapid tests for Malaria, which throughout the tropics and sub-tropics worldwide. There are similarly no rapid tests for Babesiosis, an emerging disease caused by the pathogen *Babesia duncani* or *B. microti*. Babesiosis is endemic to the US, particularly New England. The transmitting vector is a tick (that also transmits Lyme disease). Though Babesiosis infection is mostly asymptomatic in healthy adults, if it is transmitted through transfusion of an infected blood unit, it may be fatal in immunocompromised, splenectomized or elderly recipients. There is no FDA-approved test to date for the disease. Numerous authors have underscored the need for screening blood donations for these parasites. The problem of transfusion-based parasite transmission is expected to gain dramatically increasing significance, owing to globalization and international travel.

Hence, there is a need for an automated apparatus capable of inspecting blood donations or blood samples for the presence of microbial or parasitic infection. Such an apparatus should be capable of rapidly testing samples in a short time-frame, with minimal human involvement.

Parasites represent a group of extremely abundant human pathogens, which is estimated to infect around one third of the world population. These diseases are source of immense suffering and millions of deaths annually worldwide. In the US alone 11 million new cases of parasitic infections are diagnosed each year. The economic burden imposed by parasitic infections is immense and impossible to calculate.

The "gold standard" for diagnosis of most types of parasites is manual identification under a microscope of stained smears of biological fluids. Most frequently, peripheral blood, is used, or in other instances, lymphatic fluid and cerebrospinal fluid (CSF). This method is laborious and requires highly trained personnel, and as a result it is typically low-throughput and expensive. Despite that, microscopic analysis remains the most sensitive and specific method for the diagnosis of many parasitic diseases, including malaria and babesiosis. According to the World Health Organization, a patient is to be certified as free of malaria after a trained technician observes no parasites by examining 100 images of a "thick" peripheral blood smear at 100× magnification.

Additional prior art methods for detecting parasites are based on immunological or PCR tests. All such methods that are in use today are either laborious and/or expensive, preventing their use in high-throughput screening applications. For example, many versions of malaria-testing "dip sticks" have recently been described. While these may be used for initial screening in remote locations, they are not usable, for example, in blood-bank screening, as their high false positive rates would result in too many parasite-free samples to be discarded. Even when immunological and PCR tests yield a positive result, the patient's blood is most often tested by the microscopic method for conformation.

The need exists for an automated apparatus capable of inspecting blood donations or blood samples for the presence of parasitic infection. Such an apparatus should be capable of rapidly testing samples in a short time-frame, with minimal human involvement.

It would therefore be desirable to provide an apparatus for rapid detection of pathogens, and especially parasites, in bodily samples, which may be used by minimally trained personnel and which provides a high throughput.

SUMMARY OF THE INVENTION

It is an object of the present invention to provide a method for automatically and rapidly detecting pathogens in human and animal bodily fluids, bodily tissues or bodily waste products. The method of the invention can be utilized to detect the presence of parasites, or other microorganisms. The method of the invention includes steps of automated microscopy and machine-vision algorithms. The method of the invention can be utilized, for instance, to detect the presence of blood parasites, such as those associated with Malaria and Babesiosis.

It is still another object of the present invention to provide an apparatus for identifying pathogens, where the apparatus includes components for automated microscopy, and machine-vision processing for performing automatic identification of pathogens.

Other objects and advantages of the invention will become apparent as the description proceeds.

The invention provides an apparatus for automatic detection of pathogens within a sample, comprising:
  a) a cartridge support frame for receiving and supporting a cartridge having a sample within or thereupon;
  b) an optical imaging system having an optical path and comprising:
    at least one light source, at least one lens, and at least one digital camera; wherein the cartridge support frame is located within or may be moved into the optical path, such that images of the sample may be captured by the at least one digital camera;
    at least one processor interacting with and activating at least one of components a)-b); wherein the processor is adapted to perform image processing using classification algorithms on visual classification features to detect one or more suspected pathogens, when present, in the sample.

The apparatus wherein the cartridge support frame is coupled to a moveable stage, movable in at least one dimension.

The apparatus wherein the optical imaging system further comprises a focus actuator for focusing upon an image.

The apparatus, wherein the optical imaging system further comprises a plurality of objective lenses of varied magnification.

The apparatus wherein the optical imaging system further comprises: at least one optical filter or at least one dichroic beamsplitters/mirror, for exciting or detecting fluorescence.

The apparatus wherein the optical imaging system further comprises an actuator to switch the optical filters or the dichroic beamsplitter/mirror in and out of the optical path.

The apparatus wherein the at least one processor performs at least one of the following:
  selecting at least one light source from among a plurality of light sources, and activating the light source;
  selecting an exposure time of a light source;
  selecting an exposure time for the digital camera.

The apparatus wherein at least one of the at least one processor outputs a result that includes at least one of the following: the presence or absence of a pathogen; the species of pathogen; the number or concentration of pathogens detected; the life stage of the pathogen; a finding of anemia; a finding of an unusual white blood cell count; and information on the quality of the sample.

The apparatus wherein the processor outputs one or more images of suspected pathogens.

The apparatus wherein pathogen is a parasite.

The apparatus wherein the processor is present in an external computer wired to at least one of the following: to one or more internal processors, and to the digital camera.

The apparatus wherein the processor is connected via a data network to at least one of the following: to one or more internal processors, and to the digital camera.

The apparatus wherein one or more images captured by the apparatus are sent to a remote server for image processing at a remote location.

The apparatus wherein visual classification features or updated images of known pathogens or other software updates are uploadable to the apparatus.

The invention provides a cartridge for supporting a sample, wherein the cartridge comprises at least one microfluidic channel upon the cartridge. The cartridge wherein the cartridge has dimensions of 25 mm×75 mm. The cartridge having a plurality of microfluidic channels, and the channels are connected to one another to facilitate simultaneous filling. The cartridge wherein the microfluidic channel has a channel height permitting only a single layer of cells to fill the channel height, thereby presenting a monolayer for imaging.

The cartridge wherein the channel is manufactured with a hydrophilic material or is treated to promote capillary filling.

The cartridge wherein the cartridge further comprises a staining reagent, present in a form selected from: a liquid, solid, a coating, and dried within the cartridge.

The cartridge wherein the cartridge further comprises with one or more anticoagulation reagents.

The cartridge wherein the cartridge comprises a secondary application orifice allowing addition of an additional reagent to the sample after sample application is completed.

The cartridge wherein the cartridge is sterile.

The invention also provides a method for automatic detection of pathogens within a sample, comprising: performing image processing of at least one digital image captured using classification algorithms, the image processing including extracting visual classification features from the image.

The method, comprising the step of obtaining one or more digital images of a sample using an automated microscopy system comprising at least one light source, at least one lens, and at least one digital camera; the images are obtained prior to image processing.

The method, wherein the sample is a slide selected from one or more of the following: a blood smear (thin or thick), a fecal smear, a lympathic smear, a cerebrospinal fluid smear, and a tissue biopsy.

The method, comprising the step of preparing a sample within a cartridge, performed prior to the imaging.

The method, wherein the cartridge is disposed of after use.

The method, wherein the cartridge is reusable.

The method, wherein the cartridge comprises microfluidic channels for creating a monolayer of cells in at least one area, in order to facilitate imaging.

The method, wherein the cartridge is filled using capillary filling.

The method, wherein the capillary filling is done by touching the cartridge to a pin-pricked digit.

The method, wherein the preparing the sample further comprises staining the sample with one or more stains.

The method, wherein the one or more stains are selected to affect a change in at least one of the following: optical absorption, opaqueness, scattering, and color of structures within a sample.

The method, wherein the one or more stains include acridine orange, and wherein a plurality of the one or more digital images are taken using configurations that allow discerning respective staining of DNA and RNA.

The method, wherein the one or more stains include Giemsa, Romanowsky or related stains.

The method, wherein the sample is anticoagulated before or after application to the slide or cartridge.

The method, wherein the sample is anticoagulated by preloading one or more corresponding reagents onto the cartridge.

The method, wherein the cartridge is sterilized.

The method, wherein the obtaining one or more digital images includes moving the slide or cartridge with respect to the automated microscopy system in order to image multiple locations within a sample.

The method, wherein the obtaining one or more digital images includes automatically focusing the sample for the digital images.

The method, wherein the focusing includes moving at least one of the following: the at least one lens, the slide or cartridge, and the at least one component of the at least one digital camera.

The method, wherein the obtaining one or more digital images employs at least one of the following: brightfield, darkfield, phase-contrast, any interference-contrast, and fluorescence microscopy and any combination thereof.

The method, wherein the obtaining one or more digital images employs a plurality of objective lenses of varied magnification.

The method, wherein the obtaining one or more digital images employs one or more optical filters or one or more dichroic beamsplitters/mirrors for exciting or detecting fluorescence.

The method, wherein the obtaining one or more digital images includes obtaining a plurality of digital images for at least one sample location and employing a plurality of microscopy methods.

The method, wherein the plurality of microscopy methods comprise different fluorescence excitations and/or emissions.

The method, wherein the obtaining one or more digital images includes a processor that interacts with and activates mechanical and optical components by performing at least one of the following:
- selecting at least one light source from among a plurality of light sources, and activating the light source;
- selecting an exposure time of a light source;
- selecting an exposure time for the digital camera.

The method, wherein the image processing outputs a result that includes at least one of the following: the presence or absence of a pathogen; the species of pathogen; the number or concentration of pathogens detected; the life stage of the pathogen; a finding of anemia; a finding of an unusual white blood cell count; and information on the quality of the sample.

The method wherein the image processing outputs one or more images of suspected pathogens.

The method, wherein the pathogen is a parasite.

The method, wherein at least one of the one or more digital images is captured at a first location and is processed using a processor located at a second location.

The method, wherein at least one of the one or more digital images is sent to a remote server.

The method, wherein the image processing or other software is updated remotely.

The method, wherein the classification features include one or more of the following: motion, size, shape, coloring, contrast, location in respect to additional biological structures, presence of internal structures, presence of extracellular structures, the aspect ratio, the optical density, florescence at predetermined wavelengths, optical birefringence, clustering behavior, and pattern matching.

The method, wherein the image processing includes searching at least one of the one or more digital images for at least one patch which is likely to contain a target in the digital image and marking it as a candidate.

The method, wherein the image processing further includes at least one of the following:
- calculating the likelihood that the at least one candidate contains a target;
- processing the candidates for finding if more than one candidate belongs to the same target, and where found, candidates of the same target are clustered together;
- tracking at least one candidate, in relation to the at least one cluster, that may belong to the cluster, and where the tracked candidate belongs, adding the tracked candidate to the cluster; determining and classifying the likelihood that the at least one cluster contains a target; and
- determining if the image contains a target, based on the classification, and thus determining if the sample contains a pathogen.

The method, wherein the searching for at least one patch which is likely to contain a target is performed using at least one of the following: pattern matching, model matching, motion detection, high florescence segmenting and clustering, and multi-frame tracking.

The method, wherein the image processing is performed using at least one of the following modules: a single frame classification cascade module; a multi-frame candidate construction module; a multi-frame candidate tracking module; a multi-frame candidate classification module; a sample classification module; a motion field construction module; an image verification module; a camera control model; and a masking module.

The method wherein the image processing is performed in an aggregated processing manner.

The method, wherein the image processing is performed on-the-fly.

The method wherein the image processing includes finding the motion vector of the background of the image of the sample, and where the motion vector is used to reconstruct the image in order to compensate for the background motion.

The method wherein the image processing identifies and discards one or more poor images.

The method wherein the location and magnification of at least one digital images are adjusted to clear ambiguities in the image.

The method wherein the image processing identifies at least one region within at least one of the digital images as a region not likely to contain a target.

The invention provides computer readable storage medium that includes software capable of performing the image processing method of the invention.

The invention also provides computer readable storage medium that includes software capable of activating the apparatus of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description and the drawings make apparent to those skilled in the art how embodiments of the invention may be practiced.

In the drawings.

DETAILED DESCRIPTION OF PREFERRED EMBODIMENTS

Figure 1:
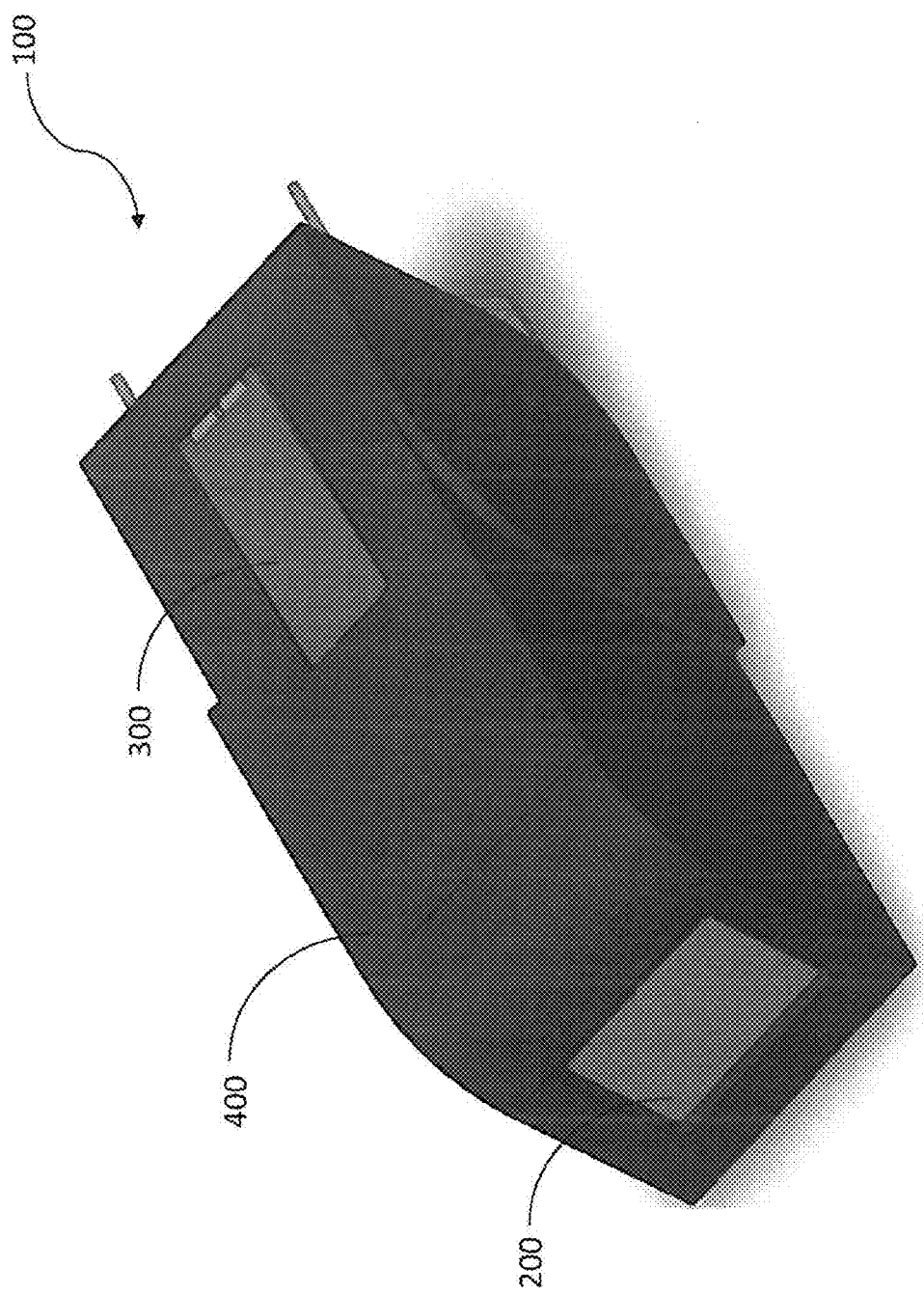
FIG. 1 is an external view of the apparatus of the invention.

In general, the present invention discloses an automated apparatus for detection of parasitic and other pathogenic infection in a bodily fluid, human tissue or human waste product.

Prior to sample testing, images of known pathogens are saved in a database, and image processing software of the invention is activated on the images to extract visual characteristics which are typically associated with each known pathogen. Classification features are constructed manually, automatically extracted or refined from a database of known pathogens, or a combination thereof.

To automatically identify pathogens within a sample, the apparatus captures one or more digital images from a sample undergoing analysis. The apparatus then utilizes image analysis software to locate putative appearances of the pathogen in the image. The apparatus compares the characteristics of a suspected pathogen present in the image, to a succinct set of characteristics extracted from images of known pathogens. The characteristics, termed "classification features" herein, may include, but are not limited to, typical motion of live parasites, their typical shape, size, their coloring, their contrast, and their location with respect to other elements of the biological sample (for example, if the pathogen is located within a mammalian cell). Additional classification features are enlarged upon hereinbelow.

The analysis is rapid, and in certain instances may be performed in less than 1 second per image or less than 2 minutes per sample.

Images taken may include still digital images, video images in digital format or simulated video images. One or more images may be utilized from each sample, as deemed necessary.

Amongst the advantages of the invention over prior art techniques are that it effectively reduces the expense, time duration, and required training for microscopic parasite detection while maintaining or exceeding the sensitivity offered by prior art gold standard methods. The sensitivity of the present invention relates, in part, to the number of images captured of various areas within the sample. By preselecting this parameter, the user can set the sensitivity as needed during a given analysis. By choosing a sufficiently large number of imaged locations, therefore, the test described herein can exceed the sensitivity of the current gold standard.

Another advantage of the invention over prior art techniques for detecting pathogens is the ability to identify the presence of several pathogens by performing a single run of the sample in the apparatus of the invention. Since the algorithm of the apparatus can contain classification features associated with several known pathogens, a single test of the sample can be sufficient to identify a wide range of pathogens.

In contrast, in prior art techniques, in order to identify, for instance, the presence of *Plasmodium*, the infectious organism for malaria, or the presence of *Trypanosoma cruzi*, the infectious organism for Chagas disease, it would be necessary to perform, for instance, one test using an antibody which identifies *plasmodium*, and a second test using an antibody which identifies *Trypanosoma cruzi*. When a multitude of patients is considered, and several pathogens are considered for each patient, the expense of multiple tests and the time consumed for diagnosis are therefore considerable.

The apparatus of the invention thus simplifies and expedites the diagnostic procedure, by using a single test in the apparatus to identify a plurality of pathogens.

As parasites, most notable *Trypanosoma brucei*, are known to rapidly mutate and become immunologically distinct from their previously known form, the invention grants an advantage over prior art techniques for identification of parasites, as the invention is not dependent upon, for instance, an antibody binding to a specific epitope that may disappear from the surface of the parasite after mutation occurs. In contrast, the invention maintains its efficacy, since parasite visual form tends to stay conserved despite rapid antigen mutation. Even if parasite visual form changes, the classification features may be updated to suitably detect the new form, and these classification features may be disseminated to all users of the invention.

Sensitivities and specificities greater than 99% were achieved using the apparatus and software of the invention on several test cases, in which a known parasite sample was analyzed in order to test the accuracy of diagnosis. This accuracy is greater than the 97% specificity achieved using prior art ELISA methods to identify parasitic samples.

For the sake of clarity the following terms are defined explicitly:

The term "cartridge" refers to a support upon which a sample of human bodily material may be placed, after which the cartridge may be inserted into the apparatus of the invention, for analysis. The cartridge may resemble a traditional slide for a light-microscope in general appearance and size, typically 75×25 mm, and is typically for a single use per sample. Alternatively, the cartridge may be a specialized sample support element, and may have dimensions of 1"×3", or may resemble a multi-well plate.

The terms "bodily material", "bodily fluid", "bodily waste product", "tissue" and "sample" are used interchangeably to refer to a material originating in the human or mammalian body, and from which a portion may be readily removed for analysis for the presence of pathogens or for visually apparent changes related to disease progression. Non-limiting examples include: blood, feces, saliva, plasma, serum, sweat, urine, milk, tears, pus, lymphatic fluid, cerebrospinal fluid, and mammalian tissues.

The term "pathogens" refers to disease causing organisms, including parasites, bacteria, fungi and viruses. In addition to detection of the pathogen itself, the apparatus of the invention can identify visual changes in bodily tissues and in fluids, which may occur as various diseases progress.

The term "classification features" refers to visually apparent characteristics of a particular pathogen or of disease progression. The classification features may be used to identify a particular pathogen. Non-limiting examples include: typical motion of a pathogen (i.e. direction and velocity), size, typical shape, coloring, contrast, autofluorescence with or without staining, derived fluorescence, the aspect ratio, internal or external structures (organelles), etc. Additional classification features are described hereinbelow.

The term "field" refers to a region of the sample supported by the cartridge that may be viewed by the microscope and camera.

The term "clip" refers to a series of images captured in rapid succession by the camera.

The term "patch" refers to a region within an image, e.g. a set of adjacent pixels, which is focused upon during processing.

When processing an image for pathogens, the term "target" refers to a real appearance of a pathogen in the image; the term "candidate" refers to a patch which, during the algorithmic processing stages, is suspected to contain a pathogen.

The term "classification algorithm" is known in the art, and refers to an algorithm that is composed of two phases. The first is the "pre-processing" training phase, during which numerous examples of the data of interest, containing both "positive" and "negative" examples are analyzed manually, automatically or in combination thereof, and a model for separating these examples is computed. In this context, a positive example is a patch depicting a pathogen, and a negative example is one that does not depict a pathogen. The actual classification takes place in the second phase. Given a novel candidate, the algorithm uses the separation model computed in the previous phase and extracts classification features to determine whether the candidate is a target or not. The first "pre-processing" step typically occurs while the apparatus is customized and configured for particular parasites, and the resulting separation model is not usually modified by the clinical user, with the exception of potential software updates. Software updates can, for example, be used to improve classification results or to introduce new diagnostic capabilities.

Central Components of the Apparatus

FIG. 1 illustrates an external view of an apparatus for detecting pathogens, according to an embodiment of the invention.

The apparatus 100 is preferably covered by a rigid casing 400, e.g. plastic or metal, for protecting the inner components of the apparatus. Apparatus 100 includes a hinged cover 300 which may be opened to reveal a cartridge support frame (best shown in FIG. 3) for receiving a cartridge upon which a sample has been applied. The cartridge support frame, for supporting a cartridge, is designed to protect the apparatus from direct contact with the tissue or sample undergoing analysis. Cartridge support frame is located such that after insertion of a cartridge containing a sample, cartridge is present within optical viewing path of microscope elements of the invention (described hereinbelow). Cartridge support frame rests on a moveable stage, and both of which can be automatically moved to capture images from different areas of the cartridge.

Display screen 200 may display the analysis results. Display screen 200 may be a touch screen, which may be used to interact with the device. In one embodiment, LCD touch screen is the "Thunderpack TAO-3530W" manufactured by Technexion™ of Taiwan, including its interface board. Alternatively, touch screen may be replaced with a display screen and keys for interaction with device.

Figure 2:
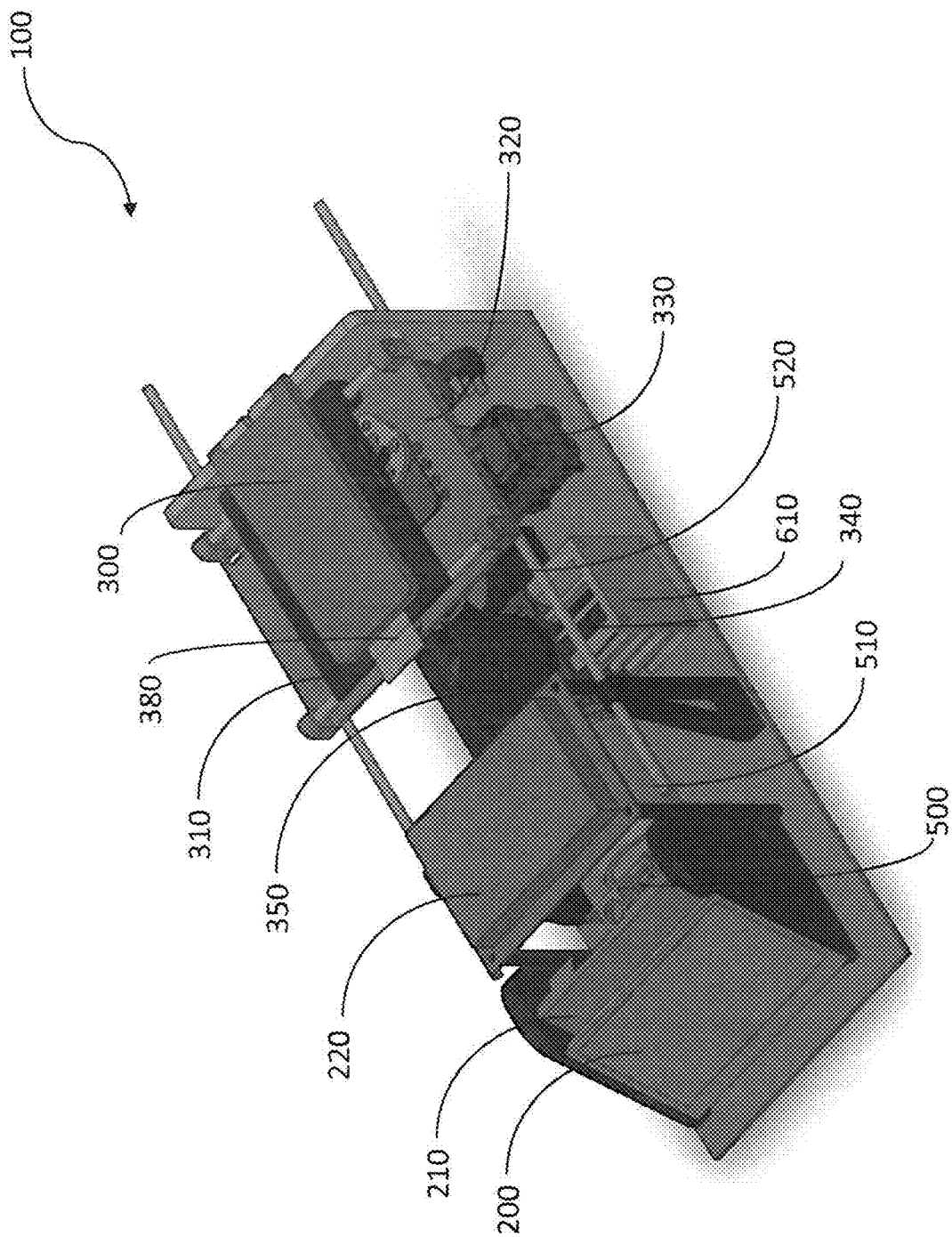
FIG. 2 is an isometric diagram of the central internal components of the apparatus.

FIG. 2 is an isometric diagram of the central internal components of the apparatus, according to an embodiment of the invention. Apparatus 100 includes touch screen 200, which is in wired communication with processor 210 and controller 220. Controller 220 may be a printed circuit board, designed to time and control the various operations of various other components.

Light source 340 is part of an optical viewing path, which includes angled mirror 520, beam splitter 350 and digital camera 500. Additional components of the optical viewing path are described in relation to FIG. 3. Optical viewing path acts to reflect an image from a cartridge undergoing analysis, after cartridge has been placed in cartridge support frame. Image is reflected towards digital camera 500.

Processor 210 is configured to receive images from the digital camera 500. Processor 210 then utilizes software of the invention to perform image analysis and compares a sample image to images stored in electronic memory, within a database of known images pertaining to known pathogens or known tissue views.

In certain embodiments of the invention, processor and controller may be a single processing unit. Alternatively, any number of processors may be included in the invention, as deemed necessary. In certain embodiments, activation of the apparatus may be controlled by an external computer, such that the processor is located in the external computer.

Lateral movement servo 330 and longitudinal movement servo (shown in FIG. 4) are configured to move the cartridge support frame 310 including a cartridge, when present, in 4 horizontal directions, thus allowing scanning of the cartridge and capturing of several images from the entire area of a cartridge.

Figure 3:
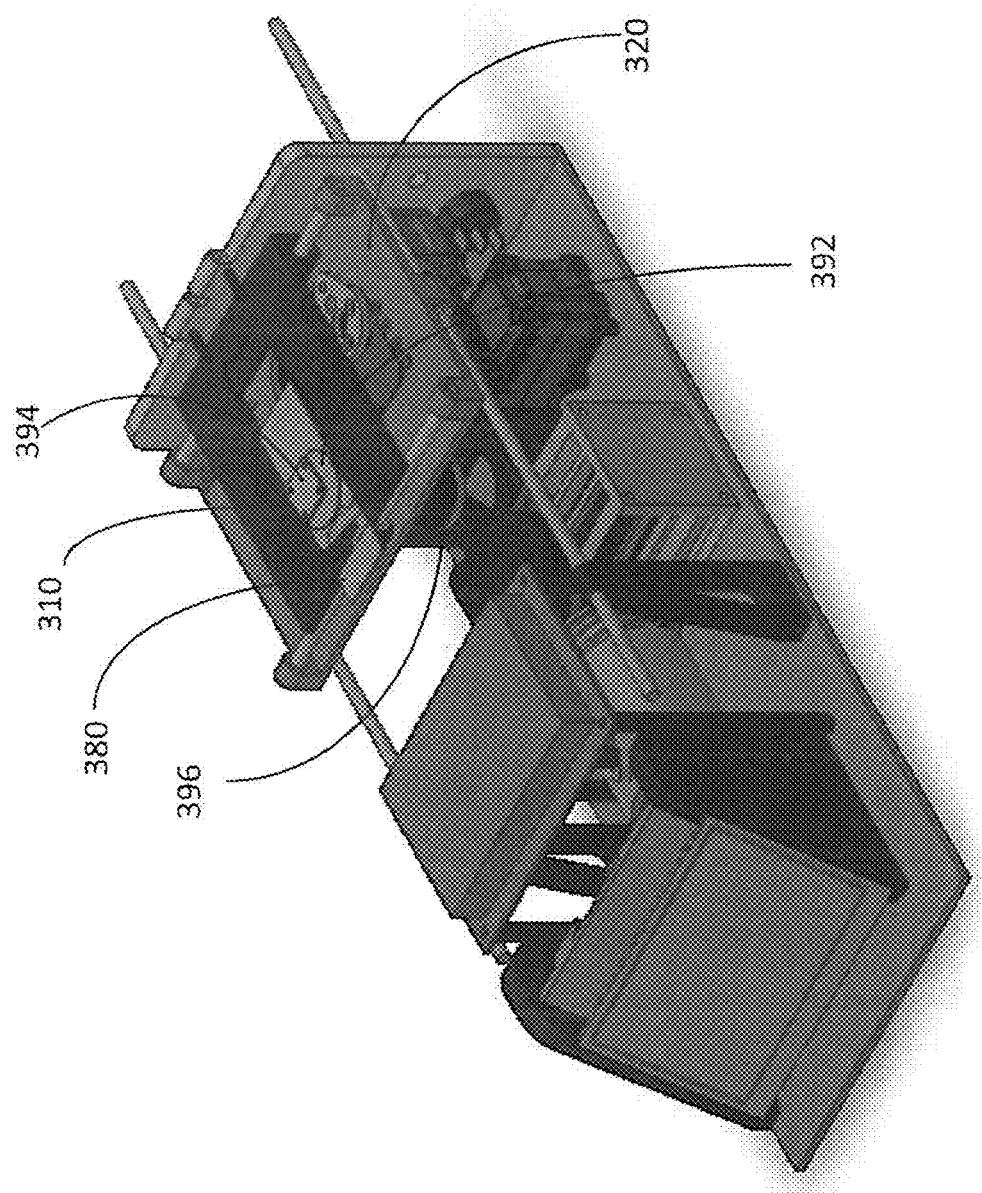
FIG. 3 illustrates a cartridge for analysis, resting within a cartridge support frame.

Referring to FIG. 3, a cartridge 380 is depicted, resting within a cartridge support frame 310. Hinged cover 300 (not shown) has been removed for ideal viewing. In this position, cartridge 380 is located within optical viewing path, as mirror 392 and LED circuit board 394 rest above cartridge 380 and are born by hinged cover 300 (not shown). Lens 396 is located beneath cartridge 380, thus focusing and continuing the optical viewing path.

Figure 9:
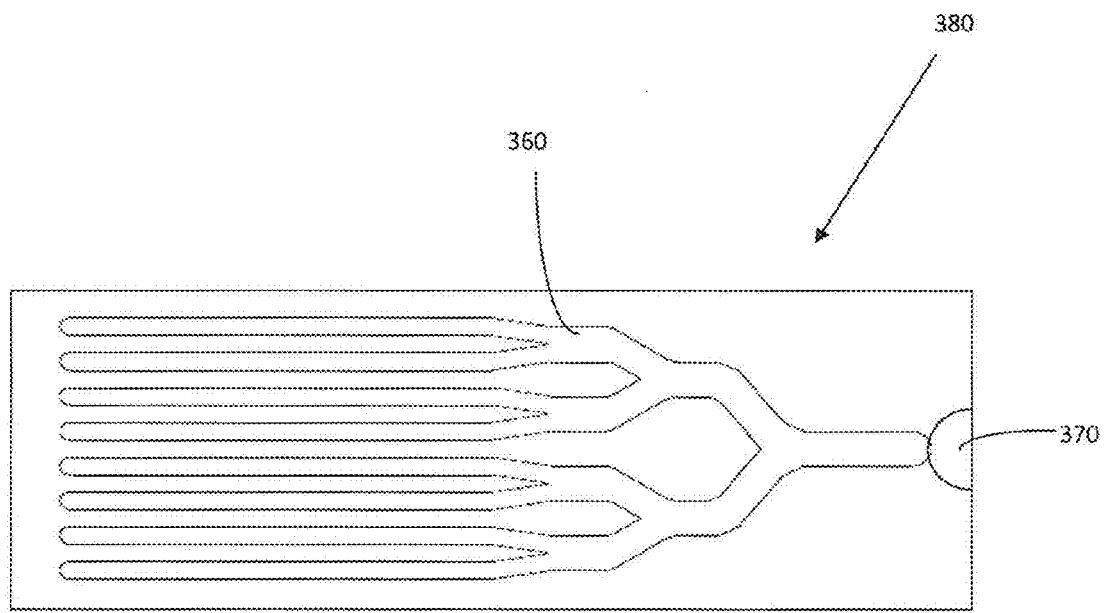
FIG. 9 illustrates an enlarged view of a cartridge.

Referring to FIG. 9, an enlarged view of the cartridge is seen. Cartridge 380 receives and supports a sample for analysis, replacing a traditional slide. After placing a sample of human bodily material upon the cartridge, the cartridge may be inserted into the apparatus of the invention, for analysis. The cartridge may resemble a traditional slide for a light-microscope in general appearance and size, typically 75×25 mm, and is typically for a single use per sample.

In the embodiment illustrated in FIG. 9, branched tracks 360 extend from an arched application recess 370. Branched tracks 360 act as microfluidic channels, to ensure diffusion of the sample over the majority of the cartridge 380 area by capillary force and can create a single layer of cells that is highly suitable for microscopic imaging. This novel cartridge design obviates the need for trained personnel to prepare the sample. Microfluidic channels typically have a maximal depth of 1 mm. The cartridge is typically disposable, however in certain embodiments it may be washed and reused.

The cartridge may additionally be pre-coated with various coatings useful for sample-preparation, such as staining, coatings for maintaining sample freshness or viability, for processing or pre-processing of the sample, and for facilitating imaging. The cartridge may be packaged to maintain the sterility and/or the quality of preloaded stains or reagents to prevent degradation during storage. The cartridge may have a secondary orifice to allow addition of another reagent after sample application has been performed.

Use of the Invention

According to a presently preferred embodiment, in use of the invention, a bodily sample is applied to the arched application recess 370 of a cartridge 380. The cartridge 380 is inserted into cartridge support frame 310, which is affixed to a moveable stage 320, and hinged cover 300 is closed.

Referring back to FIG. 2, the controller 220 will activate light source 340, to emit a light beam to illuminate the cartridge. The light beam may be emitted from one light source or a number of different light sources each emitting light beams of different wave lengths, or a combination thereof. Light source is located internal to light source heat sink 610.

Figure 4:
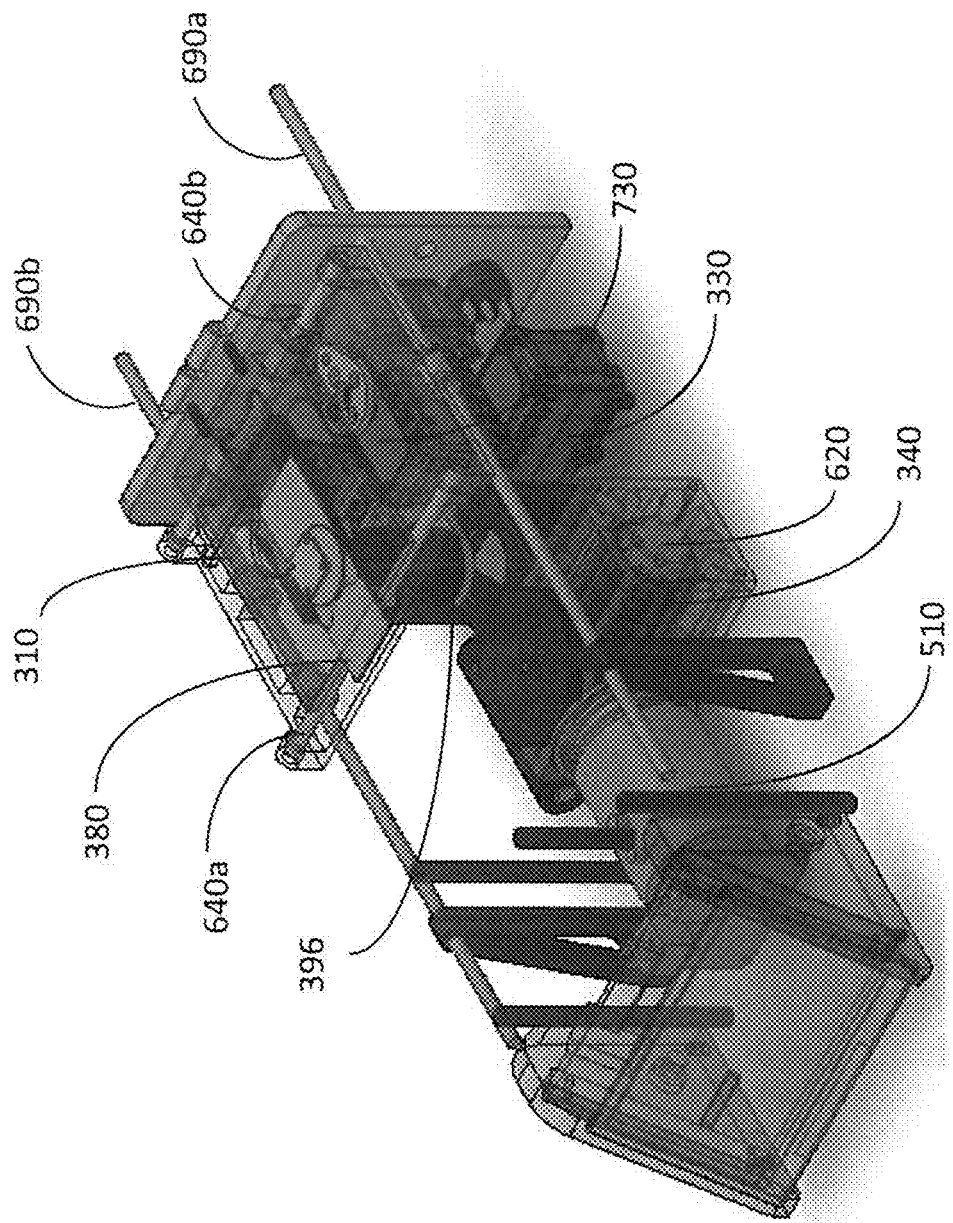
FIG. 4 is an isometric view is shown, in which upper components have been removed for optimal viewing of the internal elements of the device.

Referring now to FIG. 4, an isometric view is shown, in which certain upper or outer components have been removed, or made transparent for optimal viewing of the internal elements of the device.

In one embodiment shown in FIG. 4, a white light source 340 and a blue light source 620 are included in the apparatus, and are manufactured by Quadica Developments Inc. of Ontario, Canada:

White light for transillumination is provided by a Luxeon® LXML-PWN 1-0120 Rebel Neutral White high power LED, producing 120 lumens of light at 350 mA, and 220 lumens at 700 mA.

Blue light for detecting epifluorescence is provided by Luxeon® Blue Rebel LED, 23.5 Lumens at 350 mA and 48 Lumens at 700 mA pre-soldered to a MCPCB base. The MCPCB base is a mounted heat sink. Additional components (not shown) may be included in the apparatus that allow florescence microscopy, such as an excitation filter, a dichroic mirror or beamsplitter, and an emission filter.

In certain embodiments, one or more of the following light sources may be used: a light emitting diode (LED), laser, halogen lamp, an arc lamp, white light, blue light, yellow light, green light, red light, ultraviolet light, and infrared light, to facilitate fluorescence and non-fluorescence imaging.

The controller 220 (shown in FIG. 2) may select from among one or more emitting light sources, in order to change the wave length of the light beam according to the requirements and needs of a specific analysis.

Similarly, the controller 220 selects the exposure time, namely how long the light source will be on, how long the shutter time of the digital camera will be, the specifics of moving the moving stage (timing and direction of movement), focus and zooming in of digital camera, adjustment of the angle of angled mirror (for adjusting angle of beam, thus obtaining a depth-perspective of the sample).

Typically, several images representing a broad area of the cartridge are then captured by digital camera 500. Controller 220 co-ordinates timing and directional movement of the cartridge support frame 310 and moveable stage 320 bearing the cartridge, with the timing of activation of light source and with image capture of the digital camera, to ensure proper sequence is maintained and to ensure images are initially captured from different areas of the cartridge. Subsequently, when images have been processed and certain areas of the sample have been tagged as requiring additional analysis, controller may move the cartridge support frame 310, may move the stage 320, or may instruct camera to zoom in on these areas, may replace or add optical filters, or may illuminate the area of interest with a different light source to gather additional information.

Digital camera may be any electronic camera. In one embodiment, digital camera was monochrome 5Mpixel 12 bit, CMOS (complementary metal-oxide-silicon) camera. Model no. BTE-B050-U, manufactured by Mightex Systems of Toronto Canada and California USA.

Camera includes a CCTV lens 510, or may have other type of lens. In a presently preferred embodiment, lens is a CCTV lens of 5 MP resolution, catalog number SV-5014H manufactured by NET of Finning, Germany.

In one embodiment, the resolution obtained was approximately 0.5 micron per pixel with a 10× objective. This resolution is sufficient to detect parasites such as $T.\ brucei$, which are typically 20 microns in length. In other embodiments, the resolution obtained was approximately 0.15 micron per pixel with a 40× objective, which is sufficient to detect parasites such as $Plasmodium\ falciparum$.

Referring still to FIG. 4, objective lens 396 is located above angled mirror 520, and below cartridge 380. Angled mirror 520 reflects the illumination from the cartridge 380 in support frame 310 to the camera 500. Optionally, the viewing path may include any of the following (not shown): a field, aperture and/or condenser diaphragm, one or more shutters, a condenser lens, a plurality of objective lenses of different magnifications, and a plurality of fluorescence filters of different optical passbands.

The digital image is then transmitted to processor 210 which is designed to process and analyze the image. The image processing techniques used for analyzing the picture are described hereinbelow in the section titled "Image Processing Modules".

Referring still to FIG. 4, lateral movement servo 330 and longitudinal movement servo 730 are depicted. Controller (not shown) can instruct lateral movement servo 330 to move the moveable stage 320, in order to scan and capture images from different areas of the cartridge (when present in the apparatus).

In one embodiment, shown in the figure, servo is "Dynamixel AX-12A Robot Actuator" manufactured by Trossen Robotics LLC of Illinois, USA. Servo includes a gear reducer, DC motor and servo regulating circuitry.

The depicted cartridge support frame 310 is born by two horizontal rods 640a, 640b fixed to the upper surface of the moveable stage 320. Moveable stage 320 is also supported by two horizontal rods 690a, 690b which are perpendicular to the upper two rods, thus it is possible to shift the cartridge when present in its support frame 310, in all 4 cardinal directions, when lateral movement servo 330 and longitudinal movement servo 730 act to slide the movable stage 320 and/or cartridge support frame 310 on the rods. In certain embodiments, moveable stage may be moved using any of the following components: stepper motor, servo motor, lead screw, belt drive and worm drive.

The controller 220 can instruct servos 330, 730, to move the cartridge in all the planar directions, either in a preset pattern or according to contemporary needs, whether for image capture of the whole cartridge or for picturing specific areas of interest on the cartridge. The images may be analyzed one by one or may be aggregated to be analyzed together. Images may be captured from each area one or more times, and may be sequential or non-sequential.

Figure 5:
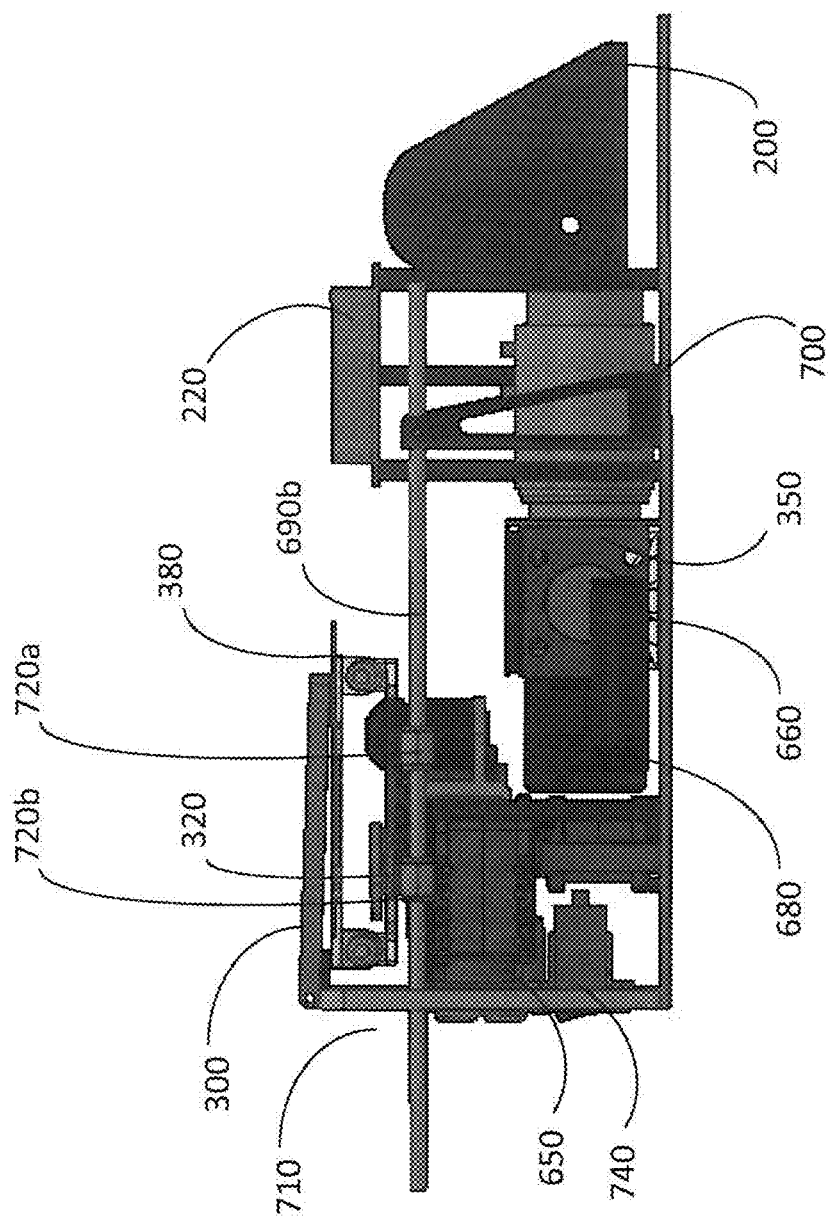
FIG. 5 is a side view of the right side of the apparatus, showing components such as the battery, base for mounting and adjusting angled mirror, support components and sliding connectors of moveable stage.

Referring to FIG. 5, an additional servo termed the "autofocus servo" 650, is a focus actuator that acts to focus objective lens.

Referring still to FIG. 5, lithium ion battery 660 is depicted, and acts to provide power to the apparatus when the apparatus is used in a remote location. Alternatively, apparatus may be connected to the electricity power grid using power inlet 670 for electrical cord, best shown in FIG. 6.

Display screen 200 is shown in side view.

Strut 700 and stand 710 support horizontal rod 690b, which extends towards moveable stage 320. Sliding connectors 720a, 720b surround horizontal rod 690b, and are fixed to moveable stage 320, allowing stage 320 to slide upon rod 690b when longitudinal servo 730 exerts directional force upon stage 320.

In a presently preferred embodiment, processor 210 stores the images obtained, in local memory, and image analysis is performed within the apparatus.

In addition the apparatus may send the images or portions thereof to be stored in an outer repository and/or analyzed on a remote computer.

Figure 6:
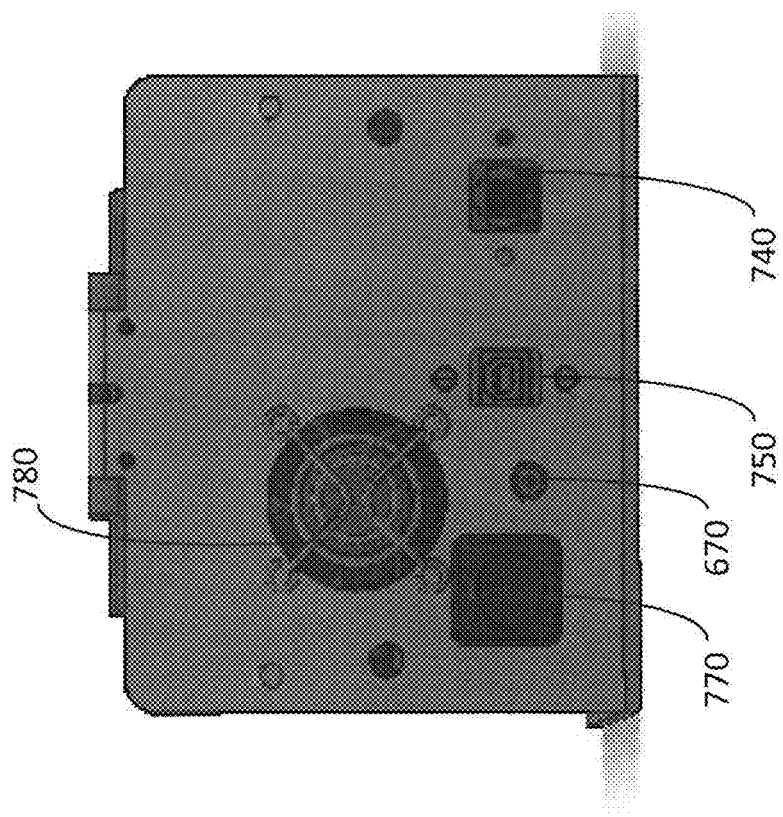
FIG. 6 is a rear view of the apparatus, showing communication ports and electrical power inlet.

Referring now to FIG. 6, for this purpose, Ethernet port jack 740 is included at the rear of the apparatus, and provides the apparatus with the option to be wired into a local area network or any other communication network for sending images obtained to a remote computer, or for communicating any other information. Optionally, remote computer may send and update images of known parasites for storing within the memory of the apparatus. USB port 750 additionally allows two way data transfer, such as of images captured.

Power inlet 670 is provided to connect the apparatus to the electrical grid, when desired. Power switch 770 is used to switch the apparatus on/off. Cooling fan 780 cools interior electrical components of the device.

The remote computer may be a central server which constantly receives images from apparatuses utilized at various locations, and server may be programmed to disseminate images of various new parasitical species to all users.

In an alternative embodiment, the images are uploaded to the remote server, where image processing and analysis is performed, and the final decision and pathogen identification is returned to the apparatus for display on the display screen.

The image processing and analysis software of the invention may be run using processing hardware that may be included in the device, or can be collocated on a standalone computer, or may be run on a remote computer in communication with the device, such as over the internet. The computer software, in turn, makes use of machine vision algorithms that detects the presence or suspected presence of parasites and optionally other information about the parasites. Some embodiments of this software are described herein below. Image analysis can take place following, alongside and/or intermittently with image capture.

An Alternative Embodiment of the Apparatus

In an Alternative Embodiment, the Apparatus Comprises the Following Central Components:

Components manufactured by Olympus Corporation (Tokyo, JP) included: microscope BX43, manual florescence illuminator BX3-URA, Trinocular tube U-CTR30-2-2, Camera adapter with C-mount, 0.5×U-TV0.5×C-3-7, Quintuple revolving nosepiece U-5RE-2, Abbe condenser U-AC2, True color LED light source U-LHLEDC, Power Cord 1.8 M UYCP, FITC filter cube U-FBW, UPLFLN20×/0.5 Universal Plan Fluorite objective with 20× magnification, and UPLFLN40×/0.75 Universal Plan Fluorite objective with 40× magnification.

Components manufactured by Prior Scientific of Rockland, Mass. USA, include:

Optiscan XYZ stage (Cat. No. ES103PS) comprising: two 10-position filter wheels (for 25 mm diameter filters), probe encoder for Z, travel XY stage, focus drive with adapter, joystick, RS232 and USB cables.

Stage insert (Cat. No. H224LP) for 1"×3"slide
Shutter 35 mm diameter, high temp (Cat. No. HF204HT)
Excitation adapter for BX/IX (Cat. No. HF235)
Emission Adapter for BX (Cat. No. HF239)
Transmitted Light adapter for BX3 (Cat. No. HF257)
Lumen 200 florescence illumination system (Cat. No. L2000L2)
Universal Stage insert for upright microscopes (Cat. No. H473UP).

Classification Features for Pathogen Identification

Central to the invention is the use of classification features which are associated with specific pathogens, in order to reach an algorithmic decision whether a pathogen is identified in the sample or not. Each pathogen is associated with specific visually identifiable classification features. These classification features can be collected when known samples are imaged using brightfield, darkfield, phase-contrast, any interference-contrast, or fluorescence microscopy. Samples can be treated to induce fluorescence, and samples can be viewed either with or without suitable staining. Non-limiting examples of classification features include:

Typical motion: certain parasites are known to move in a specific directional course, and at a typical speed.
Size.
Presence of intracellular structures associated with the pathogen (e.g. nucleus, kinetoplast, granularity).
Extraceullular structures associated with the known pathogen (e.g. flagella, knobs).
Location with respect to other sample elements (e.g. whether suspected parasite is within a red blood cell).
Aspect ratio: the ratio between the length/width of suspected structures.
Optical density (intensity shade).
Florescence in various channels: each pathogen is associated with specific florescence which can be viewed upon illumination and emission-filtering at predetermined wavelengths.
Optical birefringence: illumination in a specific wavelength results in detection of internal structures in certain parasites.
Clustering behavior: parasites maintain typical distances between one another within the human body.
Distance from human cells to suspected pathogen: Typically, pathogens maintain a predetermined distance between themselves and human cells.
Pattern matching: general appearance of pathogen.

In a presently preferred embodiment, the set of classification features is relatively small for each known pathogen, thereby their use for classification of a suspected pathogen is efficient and rapid.

Sample Preparation and Image Capture

The method and apparatus may be used on biological samples from various tissue sources or their combinations. These sample materials can include but are not limited to blood (peripheral or otherwise), lymphatic fluid, cerebrospinal fluid (CSF), urine, fecal matter, saliva, and tissue biopsies (for example, muscle, liver, etc.)

The biological sample is prepared for imaging using methods known in the art, such as thick or thin peripheral blood smears, or using a cartridge as presented herein.

The sample may be stained with a sample-appropriate stain, before the sample is applied to the slide or cartridge, for example acridine orange may be added to peripheral blood samples. Alternatively, the sample may be stained after application to the slide or cartridge, for example by dipping a thin or thick smear preparation into a stain. Optionally, a staining reagent may be present within the cartridge. Certain samples are best analyzed without undergoing staining.

Images are obtained using one or more imaging modalities to illuminate the sample, including for instance, brightfield, darkfield, phase-contrast, any interference-contrast and fluorescence microscopies. One or more optical filter combinations may be included in the device, and used for example, in excitation and emission light paths. One or more light sources may be used. One or more magnification powers may be utilized, and images may be obtained at one or more locations within the sample. Images may be captured using one or more focus depths for each sample or for each imaging location.

Fluorescence microscopy offers unique advantages in the context of the invention. Most notably, by employing a suitably chosen fluorescent staining or by imaging suitable autofluorescence channels, the resultant images can emphasize pathogen markers. For example, when blood is stained with acridine orange, fluorescence images reveal only white blood cells and parasites, due to their nucleic-acid content; red blood cells remain invisible. Such emphasis can greatly ease the computation burden on machine-vision algorithms. Furthermore, fluorescence and autofluoresence permit the identification of defined sample or cell components (such as DNA, RNA, or cell membranes). This significance can be used to inform machine-vision algorithms, thereby yielding substantially improved results.

Microscopic imaging can take advantage of autofocus capabilities. These can be implemented, for example, by providing the objective (or potentially any other lens in the optical path) with an actuated stage, actuating the sample support stage in the optical direction or by providing focus control in the camera. Focus information for the control of such actuators can be computed based on captured image sharpness, which may optionally be automatically obtained for this purpose, or with a hardware-based autofocus system, such as one based on laser return (e.g. Prior Scientific LF210). In other embodiments, the invention can take advantage of objectives with high depth of fields or with one of a number of computational and hardware techniques to extend depth of field that are known in the art ("Extended depth of field" methods).

Different embodiments may take advantage of one or several stains or staining methods. These methods may result in a change in optical absorption, opaqueness or scattering, and may influence the color or fluorescence observed in the sample. Some stains include but are not limited to; acridine orange, Giemsa stain, Romanowsky stain, Leishman stain, H&E stain, Jenner stain, Wright stain, Field stain, silver stain, Papanicolaou stain, Sudan stain, Masson's trichrome, Gram stain, eosin, orange G, DAPI, Ethidium bromide, Hoechst, SYBR stains, and other nucleic acid stains. In addition, the components, partial compositions or the combinations of these stains are possible. Some stains and combinations may produce effects in multiple imagining modalities: for example, Giemsa stain produces both a color that is visible in brightfield microscopy and a fluorescence signature that is visible in epifluorescence microscopy. In another example, while eosin is typically used for its chromogenic effect, it also carries a distinct fluorescent signature, which can be advantageous.

In particular embodiments, single or multiple stains can be imaged for fluorescence using one of more excitation wavelengths and imaged using multiple emission filters to yield multiparametric image data. For example, samples stained using acridine orange can be illuminated using blue fluorescent excitation (e.g. wavelengths 460 nm to 495 nm) and imaged, either sequentially or simultaneously, using an emission filter or filter combination for yellow-green light (e.g. bandpass filter for 515 nm to 535 nm) and an emission filter or filter combination for red light (e.g. longpass filter for 600 nm and up). In this case, the yellow-green filtered image corresponds roughly to sample DNA content, whereas the red filtered image corresponds roughly to sample RNA content. Such multiparameteric biologically-meaningful data can be used to identify various parasites, using the software algorithms of the invention.

In the preferred embodiment, multiple fluorescence images are obtained in part by mechanically switching optical filters and/or dichroic beamsplitters/mirrors in and out of the optical path. In other embodiments, the optical path is split at least once using dichroic or partial beamsplitters/mirrors and multiple fluorescence images (or fluorescence and non-fluorescence images) are obtained on multiple cameras. In the preferred embodiment, the one or more cameras are high-sensitivity CMOS cameras, such as those based on the Aptina/Micron MT9P031 sensor family. In alternative embodiments, any of the cameras can be CCD, cooled CCD, intensified CCD, or electron-multiplied CCD.

A cartridge or a traditional slide is used to support the sample for analysis within the apparatus of the invention. The cartridge is intended to simplify sample preparation, and is the presently preferred embodiment. Correspondingly, in particular embodiments, the cartridge may be designed to present a single layer of cells in order to ease microscopic imaging. Use of a cartridge presents an improvement over prior art, since prior art sample preparation is known to require training, experience and time. For example, thick blood smears typically take over an hour to dry, whereas thin blood smear require significant operator skill in order to yield large useful area. The cartridge may be disposable or reusable. In particular embodiments the cartridge has dimensions similar to a typical microscope slide, 1"×3" or 25 mm×75 mm. In a preferred embodiment, the cartridge has one or more fluidic or microfluidic channels, which may optionally be connected to each other to facilitate simultaneous filling. These channels may be comprised of at least one section with a channel height that permits only a single layer of cells to fill it, hence presenting a monolayer for imaging. In the preferred embodiment, the channels may be designed for capillary filling, for example, by choice of materials, coatings or postprocessing, as is known in the art. In certain embodiments the cartridge may be prefilled or pretreated with a staining reagent or reagents, which may be stored as a liquid, solid, a coating or dried within the cartridge. In particular embodiments, the cartridge is preloaded or pretreated with one or more anticoagulation reagents. In some embodiments, stains and/or anticoagulation reagents are added to the sample before loading onto the cartridge. In some embodiments the cartridge is sterile or sterilized. In particular embodiments, the cartridge is packaged to maintain the sterility or the quality of preloaded stains or reagents to prevent degradation during storage. In some embodiments, the cartridge permits washing, staining or otherwise treating the sample using reagents that are provided externally or that are preloaded.

In some embodiments, the sample may be prepared, loaded onto a cartridge or microscope slide, or stained using one or more automated instruments. Each such instrument may either be separate from or may be included in the apparatus of the invention. For example, the apparatus may employ a Prior Scientific™ PL200 slide loader to automatically load microscope slides of cartridges with a microscope-slide form factor of 1"×3". Alternatively, the slide loader may be modified to additionally dip the slide into appropriate staining and washing solutions.

In one embodiment, a sample of 10 μl is sufficient in volume for analysis. In case of a blood sample, a finger prick can be utilized to obtain this minute quantity, with blood being collected into a capillary, thus obviating the need for trained blood technicians for taking a sample from a patient. The capillary can then be brought into contact with the cartridge to apply the blood sample to the cartridge.

Suitable processors for implementation of the invention include, by way of example, both general and special purpose microprocessors. Generally, a processor will receive instructions and data from a read-only memory and/or a random access memory.

The apparatus may include one or more mass storage devices for storing data files (such as images obtained or images of known pathogens). Such mass storage devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks.

After the analysis is completed, the cover 300 may be opened and the cartridge may be taken out and disposed of, after which, the apparatus 100 is ready for a new analysis. Sample removal can be automated, for example, using a Prior Scientific PL200 slide loader.

Image Processing Modules

A number of modules are described below for processing an image and finding pathogens. The apparatus described above may utilize one or more of the following image processing modules. In one embodiment the apparatus invokes the following modules in a preset sequence. The following description is a presently preferred order of the processing steps, although alternative embodiments may use a different order:

1. Parasite Candidate Detection Module:

This module scans an entire image, which depicts a field within the sample, and searches for patches in the image within which it is likely that a pathogen of interest, referred to hereinafter as the "target", appears. One or more of the following methods may be used to detect these candidate patches:

a. Pattern matching—if the general form of the target is well defined, a pattern describing this form is constructed in a pre-processing stage: numerous examples of its form are manually collected, and the general pattern is extracted. When processing an image, this pattern is then matched at every location, and those locations which exhibit high similarity to the pattern are taken as candidates. In an example of preprocessing, a human operator collects a number of images, containing a known target microorganism, and marks the target on these images. Then these marked images are fed to a processor adapted to extract the general pattern of the target, based on the numerous images of the target. This pattern matching module, which is invoked by the apparatus, can use the resultant pattern of the target for finding other similar patterns in the image. The threshold of high similarity may be flexibly defined using trial and error, which may be steered by the application, or it may be defined rigidly as a pattern which has 90% similarity to the general pattern of the pathogen. Various image-processing filters (e.g. wavelettes) may be applied to enhance the features in the image which are relevant to the target's pattern and suppress those which are not. For example, when seeking pathogens which are well defined by their boundary, an edge-avoiding wavelette may be used to smooth out noise, while keeping the sharp features of the pathogen's boundary.

b. Model matching—if the general pattern of the target can be described by a simple model of a few image parameters (e.g. a blood cell can be described by a circle or an ellipse), patterns of this model are sought out in the image. In one embodiment, Hough transform may be used to transform the image into the parameter space, and parameter sets which gain support from numerous pixels are taken as candidates.

c. Motion detection—Using the Motion Field Detection Module (described below) the image can be segmented into pixels which are part of the ambient motion field, and pixels which move differently, i.e. move in other directions. The latter are clustered together spatially. The clustering algorithm takes into account the form and movement of the desired target. Clusters which confer to the characteristics of the target, such as size, are taken as candidates.

d. High fluorescence—The fluorescence image, which roughly overlays the intensity image, is segmented and clustered in a manner analogous to the motion detection above. Instead of looking for patches which move differently from the background, patches whose fluorescence is higher than the background, e.g. patches having high SNR, are sought. High fluorescence can refer to high fluorescence intensity values, or high sum fluorescence, e.g. as integrated over an area.

e. Multi Frame—Using the Tracking Module (described below), multi-frame candidates (described below as well) are tracked to frames in which they are likely to appear. If the tracking is successful, the location to which the candidate was tracked is taken as a candidate in that frame.

Note that this can be done in batch or on-the-fly. In a batch implementation, multi-frame candidates are tracked to temporally-adjacent frames, leading to new candidates. This is done iteratively to enhance the construction of multi-frame candidates.

In an on-the-fly implementation multi-frame candidates are found and processed as the images are being streamed into the processing device. They can be tracked only forward in time, and the process is performed only once.

The second step of the sequence may be:

2. Single Frame Classification Cascade Module: may also be called "Multi Frame Classification Cascade Module".

This module receives candidates, from the first step, in a single frame, and computes the likelihood that they indeed contain an occurrence of the desired target. The main tool used in this module is a Classifying algorithm. Classifying algorithms are machine-learning algorithms which may operate according to the following techniques used in sequence:

a. A set of "classification features"—functions of the data to be classified—are determined. Therefore, these classification features must be relevant to the objects which are being classified. In our case these classification features may include the intensity and gradient of the candidate, the fluorescence of the candidate and/or motion of the candidate. Additional classification features are described hereinabove, in a separate section. The images are then processed to create rotationally-invariant images, to make the classifying features independent of the viewing angle.

Magnification also affects the type of classification features used. In low magnification, the contour of the microorganism is an important hint, while in high magnification, finer details, such as pathogen-specific internal or external structures, are used.

b. In a pre-processing stage, the classifying algorithm is "trained" to differentiate between sets of classification features which describe the target and sets which do not. This is done in a so-called supervised manner, where clips in which all occurrences of the desired target are manually tagged. The Parasite Candidate Detection Module is then used on these clips. The candidates the module outputs, along with their manual tags, are used as input to train a maching-learning algorithm, such as a Support Vector Machine (SVM). An SVM is a known classifier, which uses tagged inputs as above to construct a separator in the features space between true and spurious candidates. Other machine-learning algorithms are known in the art.

c. When processing new data, the same set of classification features is extracted. The machine-learning algorithm, such as SVM, determines the likelihood of this set representing a true occurrence of the target using the separator constructed in the pre-processing stage.

The Single Frame Classification Cascade Module may employ a cascade of classifying algorithms. Candidates which are found to be highly likely to contain a target are passed to the next classifying algorithm. This cascade allows using more powerful (and computationally intensive) classifying algorithms along the cascade—the fewer candidates remaining, the more powerful the classifying algorithm can be, while maintaining reasonable running times. Importantly, the pre-processing training of a classifying algorithm is done on the output of the previous classifying algorithm up the cascade.

In addition to classifying candidates, the Single Frame Classification Cascade Module may also align them to canonical coordinates. This augments and complements the selection of rotationally-invariant features, allowing some flexibility in the latter. That is, classification features which are not invariant to rotation are still sometimes used, and the alignment phase rotates the patches to a canonical angle.

For example, when seeking the appearance of the ring-form of the malaria pathogen *P. falciparum*, it may be important that the ring form appears roughly in the same relative position within the patch. Candidates which pass the entire cascade are called "single-frame candidates".

In an alternative embodiment, classification features and/or the separator may be determined or modified manually or with non-machine-learning analysis algorithms. For example, the human expert knowledge of a trained medical professional may be transcribed into classification features or separator algorithms that may be used independently or to supplement machine-learning based processing.

In some embodiments, such as when parasite motion is of diagnostic value, the third step of the sequence may be:

3. Multi-Frame Candidate Construction Module:

This module clusters together appearances of the same target in multiple frames.

Single-frame candidates may be matched to other such candidates based on their location in the image. If the target is relatively static, then candidates are matched if they are roughly in the same location in the image (or, more precisely, in the same relative location within the motion field). More generally, if the target is moving, it is tracked using the Tracking Module (described below), and is matched to candidates appearing in roughly the same location to where it is tracked.

In effect, the Multi-Frame Candidate Construction Module constructs a graph with the single-frame candidates as its vertices, and matches defining edges. Connected components within this graph are checked for coherency, i.e. that the target appears "the same" in all occurrences. In an iterative implementation, temporal gaps within these components may be filled by extrapolating the locations of missing occurrences, and processing them with the Single-Frame Classification Cascade Module. In this case, the entire set of single-frame classifying algorithms may be used, rather than conditioning on pervious results, since only a small number of candidates are processed this way.

The coherent, and possibly gap-filled, backbone of the connected components is the multi-frame candidate—a collection of all single-frame appearances of a specific target along with the results of its classification cascade.

The other steps of the sequence may be:

4. Multi-Frame Candidate Tracking Module:

Partially-constructed multi-frame candidates may be tracked to frames temporally-adjacent to the ones in which their single-frame constituents were identified in the previous step. This can be done by various computer-vision algorithms, such as mean-shift or differential methods.

The purpose of this module is twofold. First, it facilitates initial candidate detection when other signals are weak. Candidates are created in location to which multi-frame candidates were tracked, as described in the Parasite Candidate Detection Module, above.

Second, tracking defines the matching of single-frame candidates, on which the construction of multi-frame candidates is based. Thus, the multi-frame construction can be seen as a form of agglomerated clustering: initially all single-frame candidates are distinct multi-frame candidates. They are then iteratively tracked, matched, and merged together into bigger clusters.

Note that in a sequential implementation tracking is done from one frame to the next, and thus multi-frame candidates are also constructed sequentially.

5. Multi-Frame Candidate Classification Module:

Once the entire set of target occurrences is determined, it may be classified as a whole. Technically, this is similar to the single frame classification, but here features from multiple images are used, as well as the relations between them (e.g. the trajectory of the target).

This module determines, for each multi-frame candidate, the likelihood that it's a true occurrence of the desired target.

6. Non-pathogen Sample Content Classification Module:

This module may be used to identify sample elements that are not the pathogens themselves but are useful in determining pathogen presence. For example, red blood cells may be identified in malaria diagnosis in order to determine whether a suspected target is located within a red blood cell. Similarly, white blood cells may be identified in order to rule out their nuclei as suspects. This module may itself take advantage of the same algorithms and modules that are described for the identification and analysis of pathogen suspects.

7. Sample Classification Module:

Based on the set of classifications of all multi-frame candidates, the sample is classified as either containing the defined microorganism or not containing it.

The following steps are auxiliary steps of the sequence:

8. Motion Field Construction Module:

The purpose of this module is to construct the image of the blood ambient background at each image-capture time point. When the blood is not moving, several frames are taken around the time point, and for each pixel taking the median value at its location.

More generally, dense optic flow may be used to determine the motion vector of the background from frame to frame, by taking the mean motion value. The background image is constructed by taking the median value of pixels in the same location relative to the background motion.

9. Image Verification Module:

The purpose of this module is to recognize and report poor samples, such as images taken from a blocked lens or damaged camera or images in which the sample does not appear at all.

This is done by verifying the values of simple image statistics (e.g. intensity, gradients), and the identification of known objects (e.g. blood cells).

10. Camera/Microscopy Control Module:

The purpose of this module is to control image capturing.

In a sequential implementation, the location and magnification can be adjusted to clear ambiguities in the image. For example, the camera can be adjusted to zoom in on a candidate, to visualize it in finer detail. Additionally, the module may control exposure, illumination parameters and aperture parameters in order to obtain optimal images.

11. Masking Module:

The purpose of this module is to identify regions in the image in which targets are not likely to occur. Such regions are ignored by the Parasite Candidate Detection Module.

Masking out image regions allows for quicker processing rate, and robustness against artifacts.

The invention is embodied in any suitable programming language or combination of programming languages, including Google Web Toolkit, JAVA, database managers and MySQL.

Each software component can be implemented in a high-level procedural or object-oriented programming language, or in assembly or machine language if desired. The programming language may be a compiled or interpreted language.

Images are entered into and saved in a database which may be any suitable database for storing data objects and metadata relating thereto. Any suitable database program may be used. In one embodiment, the database is a relational database and a key/value database. In one embodiment, database is a modified relational database. The search logic used for subsequent retrieval of experiments from the database, is any suitable step, process, function or series of steps, processes and functions known in the art for searching a database.

The software of the invention may include a graphical user interface (GUI). The contents of the screens, the functionality of the system and the work process may be adjustable to a user's needs. The screen designs, terms and work process reflect the medical field and are user-friendly since they display and interact with the user in syntax familiar to medical technicians. Thus use of the system may appear intuitive.

The final analysis result, which is displayed onscreen, may include the presence or suspected presence of parasites, as well as parameters regarding parasites detected, such as: their type or species, parasite load or number, life stage or maturity and any other medically relevant information. In addition, the software may report medically pertinent information obtained from the biological sample yet unrelated to parasites, (such as detection of anemia, or detection of an unusual white blood-cell count). Information relevant to the quality of the test or sample may be displayed.

In alternative embodiment, it may be desirable to have a user verify the analysis result or authorize the last step of the analysis. In such cases, this can correspond to providing images corresponding to detection of suspected pathogens, in the final result. In other cases, the separator or separator may be configured such that the provided images are only highly enriched for potential pathogens, enabling the user to make a determination based on a condensed subset of information. In these latter cases, the algorithm can be tuned to provide very high sensitivity at the cost of lower specificity.

EXAMPLES

Example 1

Detection of *Trypanosoma Cruzi* or *Trypanosoma brucei*

*Trypanosoma Cruzi* is the parasite responsible for the potentially fatal Chaggas disease. One of its life cycle stages (Trypomastigotes) occurs in the blood, where it has a worm-like shape—an elongated body and a flagellum—which constantly twirls and spins in the blood. This motion is the cue for the detection algorithm.

Human African trypanosomiasis, also termed "African Sleeping Sickness", is caused by trypanosome parasites *Trypanosoma brucei*. There is NO immunological or genetic laboratory test for identification of the parasites to date. The software of the invention successfully identified the trypanosome parasites by tracking motion of pixels within successively captured images, in a peripheral blood sample, thus identifying typical motion associated with trypanosome parasites.

Figure 7:
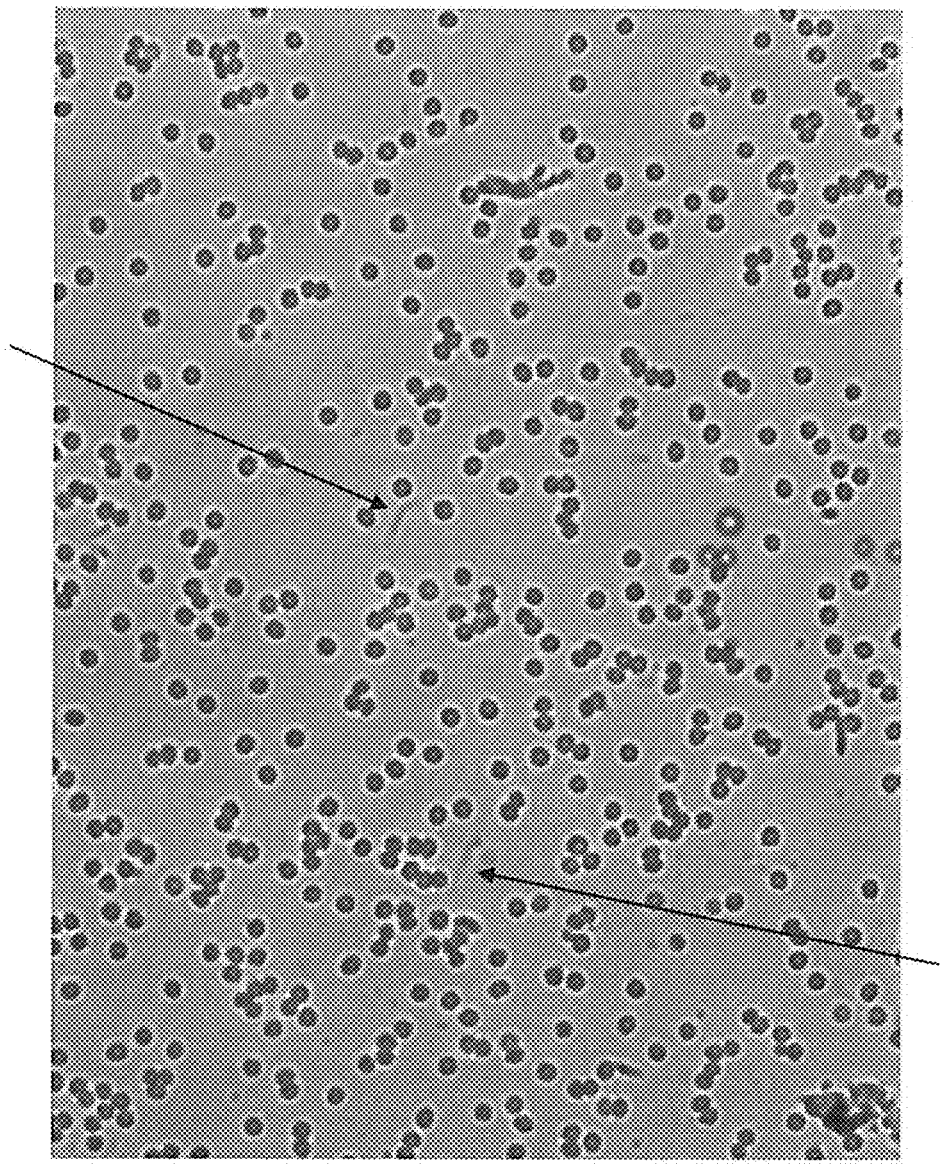
FIG. 7 is an image captured showing *Trypanosoma brucei* parasites in a peripheral blood sample, for analysis using the invention.

Referring to FIG. 7, an image captured shows *Trypanosoma brucei* parasites (indicated by arrows), surrounded by red blood cells.

Figure 8:
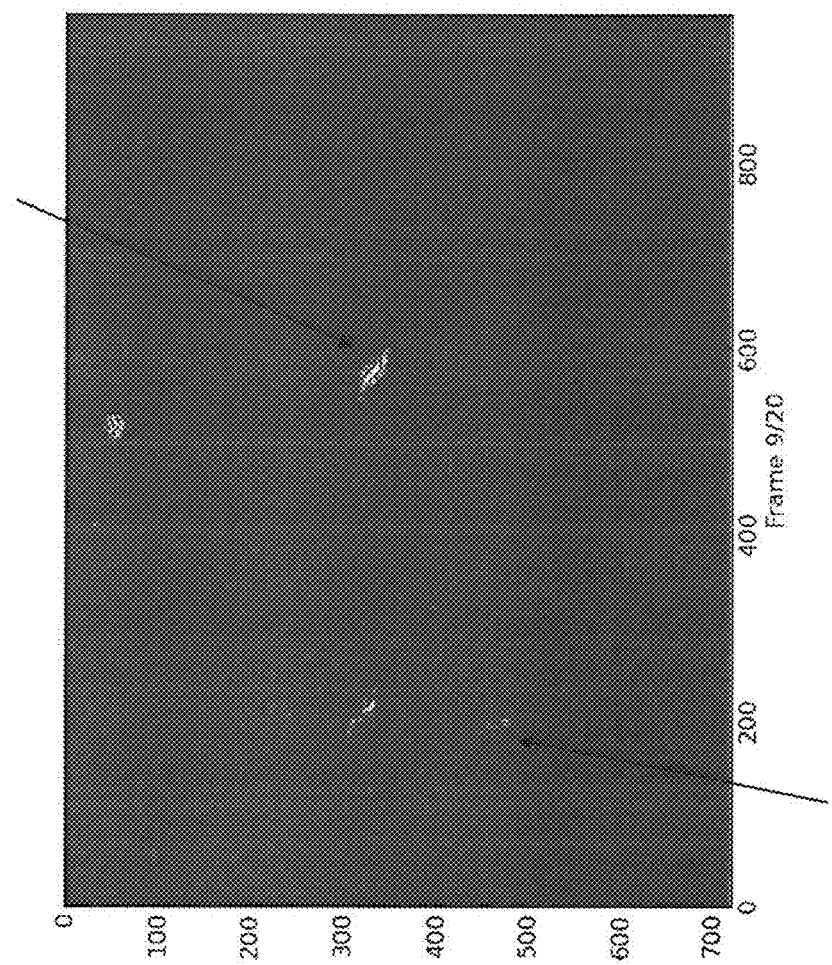
FIG. 8 is a florescent image of *Trypanosoma brucei* parasites. Automatic detection of the parasites was successful using the apparatus of the invention.

Referring to FIG. 8, after the sample was dyed fluorescently the algorithm successfully tracked motion of florescent particles (indicated by arrows), and correctly identified this motion as typical in speed and direction to trypanosome parasites. An identification of trypanosome parasites was displayed onscreen.

Using the Detection Algorithm:

1. Prepare thin blood smears upon a cartridge, and capture images. Divide the images into fields of images. Analyze each field independently by recording a series of images from that field, effectively creating a clip of images.
2. For each frame, verify its validity using the Image Verification Module. If more than a specified number of consecutive images are poor (e.g. 4 images), report an error on this field.
3. Normalize the image to compensate for lighting variance, since typically the image is more strongly illuminated at its center.
4. For each frame in the clip, construct the background image using the Motion Field Construction Module. In thin blood samples it is possible to wait for the red blood cells to dry in order to use the simpler version of the algorithm.

5. Create initial single-frame candidates using the Motion Detection method of the Parasite Candidate detection Module.
6. Proceed to the next frame:
    1. Use the Multi-Frame Candidate Tracking Module to track the single-frame candidates to the next frame,
    2. Repeat steps 2-4 above for the next frame.
7. Use the Multi-frame Candidate Construction Module to match candidates from one frame to the next one.
8. Classify candidates which were matched for at least a specified fraction of consecutive frames (e.g. 3 of 4 frames) using the Multi-frame Candidate Classification Module.
9. Record the number of candidates classified as "true" targets (an appearance of *T. Brucei*), over all fields.
10. Determine if the blood sample is contaminated using the Blood Sample Classification Module.

Using the Training Algorithm—Single/Multi-Frame Candidate Classification Module:
1. Run the detection algorithm up to step 6
2. Tag the candidates as "true" and "false" occurrences of *T. Brucei*.
3. Create a database of false and true occurrences. In the database each occurrence appears multiple times, e.g. 12, by uniformly rotating it.
4. Extract classification features for each database entry. For example, compute a Census Transform of the entry: divide the result into equal-sized rectangular regions (e.g. 9 non-overlapping squares) and compute a histogram of the census transform in each region. The feature vector for the entry is a concatenation of these histograms.
5. Train an SVM classifier with a polynomial kernel (e.g. a $2^{nd}$ degree polynomial) on this database.

Using the Training Algorithm—Blood Sample Classification Module:
1. Run the detection algorithm up to step 9.
2. Tag each sample as "clean" or "contaminated".
3. Create histograms of the number of "true" candidates over the "clean" samples and over the "contaminated" samples.
4. Determine the optimal value that differentiates between these two histograms (in the sense of maximum likelihood). This value determines how a blood sample is classified in the detection algorithm.

Example 2

Detection of *Plasmodium* and *Babesia* Species

*Plasmodium* are parasites responsible for Malaria disease; *Babesia* are parasites responsible for Babesiosis disease. Both types of parasites infect red blood cells (RBCs) and in the initial stages of the infection form ring-like structures. Importantly, normal RBCs expel their organelles, and in particular their nucleus, before entering the blood stream. Hence the goal is to detect RBCs which contain a significant amount of DNA, indicating parasitic infection of *Plasmodium* or *Babesia*.

*Plasmodium* and *Babesia* species of interest include *P. Falciparum, P. Vivax, P. Ovale, P. Malariae, B. Microti* and *B. Divergens*.

Detection Algorithm:
1. Initially, the blood is stained with fluorochromatic dyes such as Acridine Orange, Giemsa or Ethidium Bromide. Dyes which stain DNA and not RNA or which create a contrast between the two, are preferable.
2. A thin blood smear is prepared upon a cartridge, images are captured, and the images are divided into fields, as explained in the first example. Each field is analyzed independently by recording two images from that field—a "bright field" (BF) image (visible light) and "florescence image" (FL) radiated with a wave length appropriate to cause the dye to fluoresce.
3. For each BF-image, verify its validity using the Image Verification Module. If more than a specified number of images are poor (e.g. >10%) report an error on this field.
4. Normalize the image to compensate for lighting variance, since typically the image is more strongly illuminated at its center.
5. For each FL-image, locate high-intensity patches, indicative of DNA using the High Fluorescence method of the Parasite Candidate Detection Module.
6. For each such patch, tag it as inside a RBC, and identify a candidate RBC, if one the following holds:
    a) A Hough Transform of its vicinity indicates that it's contained inside a circle in the image whose size is appropriate for a RBC. This is, effectively, the use of the Model Matching method of the Parasite Candidate Detection Module.
    b) A contour detection algorithm of its vicinity indicates that it's within a convex shape in the image, whose size is appropriate for a RBC.
    c) The Pattern Matching method of the Parasite Candidate Detection Module processing the patch's vicinity locates a strong RBC pattern overlapping the patch.
7. Using the Single-frame Classification Cascade Module, each candidate RBC is classified as to whether or not it's a RBC containing a parasite.
8. Record the number of candidates classified as "true" (an appearance of an infected RBC), over all fields.
9. Determine if the blood sample is contaminated using the Blood Sample Classification Module.

Training Algorithm—Single-Frame Candidate Classification Cascade Module:
In this embodiment, there is no true cascade, just a single classification algorithm.
1. Run the detection algorithm up to step 6
2. Tag the candidates as "true" or "false" occurrences of infected RBCs.
3. Create a database of false and true occurrences. In the database each occurrence appears multiple times, e.g. 12, by uniformly rotating it.
4. Extract classification features for each database entry. For example, compute the Census Transform of the entry; divide the result into equal-sized rectangular regions (e.g. 9 non-overlapping squares) and compute a histogram of the census transform in each region. The feature vector for the entry is a concatenation of these histograms.
5. Train an SVM classifier with a polynomial kernel, e.g. a $2^{nd}$ degree polynomial, on this database.

Training Algorithm—Blood Sample Classification Module:
1. Run the detection algorithm up to step 8.
2. Tag each sample as "clean" or "contaminated".
3. Create histograms of the number of "true" candidates over the "clean" samples and over the "contaminated" samples.
4. Determine the optimal value that differentiates between these two histograms (in the sense of maximum likelihood). This value determines how a blood sample is classified in the detection algorithm.

In summary, the apparatus and method of the invention answer a long-felt need for automatic identification of pathogens, and especially of parasites within a mammalian sample. The apparatus and method allow rapid identification of parasites that previously required use of expensive resources and trained personnel that are unavailable in many third world countries. The invention now allows blood donations and blood tests to be screened for parasites, such that a single run through the apparatus will identify a great many parasites, representing maximal efficiency. The apparatus and method overcome the difficulty of parasites constantly evolving, as an image of the new species may be easily uploaded into the database of known images and the characteristics of the new species may be analyzed to allow its identification in future.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the invention or exceeding the scope of the appended claims.

The invention claimed is:

1. A method of automatic detection of *plasmodium* within a sample comprising:
   obtaining, for each of a plurality of fields, at least three digital images of a sample stained with a combination of acridine orange and Hoechst for differential staining of DNA and RNA, wherein the images are obtained under at least two different lighting conditions, including a brightfield lighting condition and a fluorescent lighting condition, wherein at least a first image is obtained under a lighting condition causing fluorescence of DNA in the sample, and at least a second image is obtained under a lighting condition causing fluorescence of RNA in the sample;
   performing image processing of the images using at least one classification algorithm, said image processing including identifying bodies showing fluorescent staining for DNA in the at least a first digital image and showing fluorescent staining for RNA in the at least a second digital image, extracting one or more visual classification features of the identified bodies, and using at least one machine-learning algorithm to determine a presence or absence of *plasmodium*; and
   outputting an indication of said determination.

2. The method of claim 1, wherein said sample is selected from the group consisting of a blood smear (thin or thick), a fecal smear, a lymphatic smear, a cerebrospinal fluid smear, and a tissue biopsy.

3. The method of claim 1, wherein the digital images are obtained at a single focus depth.

4. The method of claim 1, wherein the digital images are obtained at a plurality of magnifications.

5. The method of claim 1, wherein the digital images are obtained using one or more optical filters or one or more dichroic beamsplitters/mirrors for exciting or detecting fluorescence.

6. The method of claim 1, wherein the digital images are obtained using a plurality of microscopy methods.

7. The method of claim 6, wherein said plurality of microscopy methods comprise different fluorescence excitations and/or emissions, thereby yielding multiparametric image data.

8. The method of claim 1, wherein said obtaining digital images includes, by a processor that interacts with and activates mechanical and optical components of a digital microscopy system, performing at least one of the following:
   selecting at least one light source from among a plurality of light sources, and activating said light source;
   selecting an exposure time of a light source;
   selecting an exposure time for a digital camera.

9. The method of claim 1, wherein said indication is indicative of at least one of the following: the presence or absence of the *plasmodium*; the species of the *plasmodium*; the number or concentration of the *plasmodium* detected; the life stage of the *plasmodium*; a finding of anemia; a finding of an unusual white blood cell count; and information on the quality of the sample.

10. The method of claim 1, wherein said outputting further includes outputting one or more images of suspected *plasmodium*.

11. The method of claim 1, wherein said one or more visual classification features are selected from the group consisting of: motion, size, shape, coloring, contrast, location in respect to additional biological structures, presence of internal structures, presence of extracellular structures, the aspect ratio, the optical density, florescence at predetermined wavelengths, optical birefringence, clustering behavior, intensity, gradient, distance from human cells to suspected *plasmodium*, and pattern matching.

12. The method of claim 1, wherein said image processing includes, for at least one image, searching for at least one patch which is likely to contain a target and marking it as a candidate.

13. The method of claim 12, wherein said image processing further includes, for at least one image, at least one of the following:
   calculating the likelihood that said at least one candidate contains a target;
   processing said candidates for finding if more than one candidate belongs to the same target, and where found, candidates of the same target are clustered together;
   tracking at least one candidate, in relation to said at least one cluster, that may belong to said cluster, and where said tracked candidate belongs, adding said tracked candidate to said cluster;
   determining and classifying the likelihood that said at least one cluster contains a target; and
   determining if said image contains a target, based on said classification, and thus determining if said sample contains a *plasmodium*.

14. The method of claim 12, wherein said searching for at least one patch which is likely to contain a target is performed using at least one of the following: pattern matching, model matching, high florescence segmenting and clustering, and multi-frame tracking.

15. The method of claim 1, wherein said image processing is performed using at least one of the following modules: a single frame classification cascade module; a multi-frame candidate construction module; a multi-frame candidate tracking module; a multi-frame candidate classification module; a sample classification module; a motion field construction module; an image verification module; a camera control model; and a masking module.

16. The method of claim 1, wherein said image processing is performed in an aggregated processing manner.

17. The method of claim 1, wherein said image processing is performed on-the-fly.

18. The method of claim 1, wherein said image processing includes identifying and discarding at least one poor image out of said digital images.

19. The method of claim 11, wherein the visual classification features which are used in the image processing, for any given digital image, depend at least in part on the magnification of the digital image.

20. The method of claim 1 wherein obtaining said digital images of the sample comprises using an automated microscopy system comprising at least one light source, at least one lens, and at least one digital camera; said digital images are obtained prior to image processing.

* * * * *